(12) United States Patent
Pisula, Jr. et al.

(10) Patent No.: US 8,448,994 B2
(45) Date of Patent: *May 28, 2013

(54) LATCH ASSEMBLY FOR JOINING TWO CONDUITS

(75) Inventors: James D. Pisula, Jr., Fort Collins, CO (US); Bruce A. Williams, Fort Collins, CO (US); Ravikumar Narayanan, Fort Collins, CO (US); Francis J. Lombardi, III, Loveland, CO (US); Robert J. Elshof, Fort Collins, CO (US); Marc Lalouette, Boulder, CO (US)

(73) Assignee: Nordson Corporation, Westlake, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/568,076

(22) Filed: Aug. 6, 2012

(65) Prior Publication Data

US 2012/0299290 A1 Nov. 29, 2012

Related U.S. Application Data

(63) Continuation of application No. 12/167,833, filed on Jul. 3, 2008, now Pat. No. 8,235,426.

(51) Int. Cl.
*F16L 37/00* (2006.01)
(52) U.S. Cl.
USPC .............. 285/308; 285/305; 285/921
(58) Field of Classification Search
USPC ................. 285/308, 305, 921, 317
See application file for complete search history.

(56) References Cited

U.S. PATENT DOCUMENTS

| 163,261 | A | 5/1875 | Ruppenthal |
| 185,896 | A | 1/1877 | Curtis |
| 187,982 | A | 3/1877 | Pirsson et al. |
| 200,944 | A | 3/1878 | Smith |
| 235,580 | A | 12/1880 | Smith et al. |

(Continued)

FOREIGN PATENT DOCUMENTS

| BE | 479098 | 1/1948 |
| DE | 1868896 | 3/1963 |

(Continued)

OTHER PUBLICATIONS

About Us [online], Thuro Metal Products [retrieved on Apr. 9, 2010], retrieved from the Internet: <URL: http://www.thurometal.com/about.html>, 2 pages.

(Continued)

*Primary Examiner* — David E Bochna
(74) *Attorney, Agent, or Firm* — Dorsey & Whitney LLP

(57) ABSTRACT

A latch assembly for connection of conduit, the assembly comprising a female portion and a male portion, wherein each of the female portion and the male portion have a shell and a connection device. The connection device of the female portion includes a connection assembly with a molded-in slot, a release button, and a raised rib or alternatively is a connection opening. The connection device of the male portion includes a cantilevered region with a ramped engagement feature or alternatively is a raised cantilevered release button. When connected the cantilevered region or button deflects to accommodate the female portion until the ramped engagement feature or button engages the molded-in slot or connection opening, thus releasing the deflection. Depressing the release button disengages the latch allowing separation of the assembly.

2 Claims, 30 Drawing Sheets

U.S. PATENT DOCUMENTS

| | | |
|---|---|---|
| 327,509 A | 10/1885 | Aldridge |
| 584,008 A | 6/1887 | Munson |
| 465,868 A | 12/1891 | List |
| 725,421 A | 4/1903 | Dinkins |
| 727,982 A | 5/1903 | Ludwig |
| 874,957 A | 12/1907 | Godley |
| 884,461 A | 4/1908 | Browne |
| 909,131 A | 1/1909 | Antic |
| 951,889 A | 3/1910 | Teuer |
| D42,368 S | 3/1912 | Mossberg |
| 1,029,819 A | 6/1912 | Nylander |
| 1,033,187 A | 7/1912 | Metzger |
| 1,039,354 A | 9/1912 | Bonadio |
| 1,077,417 A | 11/1913 | McCracken |
| 1,078,112 A | 11/1913 | Storm |
| 1,115,945 A | 11/1914 | Kunz |
| 1,193,446 A | 8/1916 | Wells |
| 1,239,345 A | 9/1917 | Brown |
| 1,255,847 A | 2/1918 | Arkin |
| 1,259,684 A | 3/1918 | Vinten |
| 1,489,310 A | 4/1924 | Critchlow |
| 1,526,218 A | 2/1925 | Johnson |
| 1,578,504 A | 3/1926 | Bronson et al. |
| 1,587,079 A | 6/1926 | Machino |
| 1,767,073 A | 6/1930 | Ingold |
| 1,863,360 A | 6/1932 | Weatherhead |
| 1,950,947 A | 3/1934 | Mulroyan |
| 2,023,428 A | 12/1935 | Liebhardt |
| 2,056,524 A | 10/1936 | Johnson |
| 2,066,473 A | 1/1937 | Jorgensen |
| 2,097,628 A | 11/1937 | Liebhardt |
| 2,099,335 A | 11/1937 | Hansen |
| 2,108,714 A | 2/1938 | Hirsch et al. |
| 2,116,705 A | 5/1938 | Marx et al. |
| 2,139,745 A | 12/1938 | Goodall |
| 2,147,355 A | 2/1939 | Scholtes |
| 2,159,116 A | 5/1939 | Zacharias |
| 2,211,147 A | 8/1940 | Miller |
| 2,257,321 A | 9/1941 | Arnold |
| 2,263,293 A | 11/1941 | Ewald |
| 2,264,815 A | 12/1941 | Thomsen |
| 2,340,119 A | 1/1944 | Graham |
| 2,346,445 A | 4/1944 | Merker et al. |
| 2,352,728 A | 7/1944 | Merker et al. |
| 2,429,782 A | 10/1947 | Versoy |
| 2,432,946 A | 12/1947 | Theunissen |
| 2,470,800 A | 5/1949 | Ashton |
| 2,479,499 A | 8/1949 | Le Clair |
| 2,500,720 A | 3/1950 | Van der Heem |
| 2,507,536 A | 5/1950 | Goodson |
| 2,516,583 A | 7/1950 | Moore |
| 2,535,740 A | 12/1950 | Knopp |
| 2,577,009 A | 12/1951 | Frantz |
| 2,626,974 A | 1/1953 | Howard et al. |
| 2,630,131 A | 3/1953 | Snyder |
| 2,661,018 A | 12/1953 | Snyder |
| 2,701,147 A | 2/1955 | Summerville |
| 2,722,399 A | 11/1955 | Oetiker |
| 2,753,195 A | 7/1956 | Palmer |
| 2,774,616 A | 12/1956 | Dodd et al. |
| 2,790,571 A | 4/1957 | Flaith et al. |
| 2,864,628 A | 12/1958 | Edleson |
| 2,915,325 A | 12/1959 | Foster |
| 2,926,934 A | 3/1960 | Gill |
| 2,931,668 A | 4/1960 | Baley |
| 2,937,892 A | 5/1960 | Prescott, Jr. |
| 2,948,553 A | 8/1960 | Gill et al. |
| 2,967,067 A | 1/1961 | Singer |
| 2,991,090 A | 7/1961 | De Cenzo |
| 3,017,203 A | 1/1962 | Macleod |
| 3,037,497 A | 6/1962 | Roberson |
| 3,046,028 A | 7/1962 | Nathan |
| 3,048,415 A | 8/1962 | Shook |
| 3,073,342 A | 1/1963 | Magorien |
| 3,078,068 A | 2/1963 | Romney |
| D196,473 S | 10/1963 | Hill |
| 3,124,157 A | 3/1964 | Krzewina |
| 3,129,020 A | 4/1964 | Bujnowski |
| 3,171,196 A | 3/1965 | Helitas |
| 3,191,628 A | 6/1965 | Kirkwood et al. |
| 3,217,400 A | 11/1965 | Illesy et al. |
| 3,217,771 A | 11/1965 | Beall et al. |
| 3,227,380 A | 1/1966 | Pinkston |
| 3,237,974 A | 3/1966 | Press |
| 3,245,703 A | 4/1966 | Manly |
| 3,276,799 A | 10/1966 | Moore et al. |
| 3,279,497 A | 10/1966 | Norton et al. |
| 3,314,696 A | 4/1967 | Ferguson et al. |
| 3,317,214 A | 5/1967 | Durgom |
| D209,166 S | 11/1967 | Hunt |
| D209,168 S | 11/1967 | Hunt |
| 3,352,576 A | 11/1967 | Thomas |
| 3,382,892 A | 5/1968 | Cerbin |
| 3,394,954 A | 7/1968 | Sarns |
| 3,403,930 A | 10/1968 | Bernier |
| 3,432,176 A | 3/1969 | Valenziano |
| 3,448,760 A | 6/1969 | Cranage |
| 3,450,424 A | 6/1969 | Calisher |
| 3,512,808 A | 5/1970 | Graham |
| 3,523,701 A | 8/1970 | Graham |
| 3,538,940 A | 11/1970 | Graham |
| 3,542,338 A | 11/1970 | Scaramucci |
| 3,545,490 A | 12/1970 | Burrus |
| 3,550,626 A | 12/1970 | Daniels et al. |
| 3,560,027 A | 2/1971 | Graham |
| 3,563,265 A | 2/1971 | Graham |
| 3,574,314 A | 4/1971 | Quercia |
| 3,588,149 A | 6/1971 | Demler |
| 3,596,933 A | 8/1971 | Luckenbill |
| 3,599,843 A | 8/1971 | Johnston |
| 3,600,917 A | 8/1971 | Krock |
| 3,649,050 A | 3/1972 | Woodling |
| 3,666,297 A | 5/1972 | Marks |
| 3,690,336 A | 9/1972 | Drum |
| 3,712,583 A | 1/1973 | Martindale et al. |
| 3,747,964 A | 7/1973 | Nilsen |
| 3,750,238 A | 8/1973 | Tanner |
| 3,815,887 A | 6/1974 | Curtis et al. |
| 3,817,561 A | 6/1974 | Kay |
| 3,829,135 A | 8/1974 | Forni |
| 3,876,234 A | 4/1975 | Harms |
| 3,889,710 A | 6/1975 | Brost |
| 3,899,200 A | 8/1975 | Gamble |
| 3,921,656 A | 11/1975 | Meisenheimer, Jr. et al. |
| 3,979,934 A | 9/1976 | Isenmann |
| 3,990,674 A | 11/1976 | Schattenberg |
| 3,995,659 A | 12/1976 | Cantore |
| 4,025,049 A | 5/1977 | Schmidt |
| 4,039,213 A | 8/1977 | Walters |
| 4,072,330 A | 2/1978 | Brysch |
| 4,099,748 A | 7/1978 | Kavick |
| 4,113,627 A | 9/1978 | Leason |
| 4,116,476 A | 9/1978 | Porter et al. |
| 4,129,145 A | 12/1978 | Wynn |
| 4,142,546 A | 3/1979 | Sandau |
| D252,470 S | 7/1979 | Pawlak |
| 4,181,149 A | 1/1980 | Cox |
| 4,182,519 A | 1/1980 | Wilson |
| D254,505 S | 3/1980 | Parsons et al. |
| 4,200,605 A | 4/1980 | Imamura |
| D255,145 S | 5/1980 | Nederman |
| 4,220,360 A | 9/1980 | Jacek et al. |
| D258,526 S | 3/1981 | Nederman |
| 4,253,687 A | 3/1981 | Maples |
| D259,278 S | 5/1981 | McCaw |
| 4,271,865 A | 6/1981 | Galloway et al. |
| 4,282,175 A | 8/1981 | Volgstadt et al. |
| 4,287,644 A | 9/1981 | Durand |
| 4,294,285 A | 10/1981 | Joslyn |
| 4,296,949 A | 10/1981 | Muetterties et al. |
| 4,319,774 A | 3/1982 | Kavick |
| 4,330,010 A | 5/1982 | Drescher et al. |
| 4,330,142 A | 5/1982 | Paini |
| 4,331,175 A | 5/1982 | Brake et al. |
| 4,331,177 A | 5/1982 | Makishima |
| 4,340,200 A | 7/1982 | Stegmeier |
| 4,345,786 A | 8/1982 | Egert |

| | | | | | | |
|---|---|---|---|---|---|---|
| 4,346,703 A | 8/1982 | Dennehey | | 5,029,908 A | 7/1991 | Belisaire |
| 4,351,351 A | 9/1982 | Flory et al. | | 5,033,777 A | 7/1991 | Blenkush |
| 4,366,816 A | 1/1983 | Bayard et al. | | D319,312 S | 8/1991 | Schneider |
| 4,393,548 A | 7/1983 | Herb | | 5,052,725 A | 10/1991 | Meyer et al. |
| 4,397,442 A | 8/1983 | Larkin | | 5,074,601 A | 12/1991 | Spors et al. |
| 4,407,526 A | 10/1983 | Cicenas | | 5,076,615 A | 12/1991 | Sampson |
| 4,431,031 A | 2/1984 | Ettlinger | | 5,078,429 A | 1/1992 | Braut et al. |
| 4,431,218 A | 2/1984 | Paul | | 5,085,472 A | 2/1992 | Guest |
| 4,434,121 A | 2/1984 | Schaper | | 5,090,448 A | 2/1992 | Truchet |
| 4,436,125 A | 3/1984 | Blenkush | | 5,090,747 A | 2/1992 | Kotake |
| 4,437,689 A | 3/1984 | Goebel et al. | | 5,094,482 A | 3/1992 | Petty et al. |
| 4,439,188 A | 3/1984 | Dennehey | | 5,104,158 A | 4/1992 | Meyer et al. |
| 4,458,719 A | 7/1984 | Strybel | | 5,106,127 A | 4/1992 | Briet |
| 4,489,914 A | 12/1984 | Stevenson et al. | | D326,155 S | 5/1992 | Boehringer et al. |
| 4,489,961 A | 12/1984 | Laidig | | 5,110,163 A | 5/1992 | Benson et al. |
| 4,500,118 A | 2/1985 | Blenkush | | 5,112,084 A | 5/1992 | Washizu |
| 4,527,745 A | 7/1985 | Butterfield et al. | | 5,114,250 A | 5/1992 | Usui |
| 4,541,457 A | 9/1985 | Blenkush | | D326,715 S | 6/1992 | Schmidt |
| 4,541,657 A | 9/1985 | Smyth | | 5,123,677 A | 6/1992 | Kreczko et al. |
| 4,553,587 A | 11/1985 | Traylor | | 5,143,381 A | 9/1992 | Temple |
| D282,962 S | 3/1986 | Gerber | | 5,160,177 A | 11/1992 | Washizu |
| 4,580,816 A | 4/1986 | Campbell et al. | | 5,160,474 A | 11/1992 | Huff |
| 4,603,888 A | 8/1986 | Goodall et al. | | 5,165,733 A | 11/1992 | Sampson |
| 4,603,890 A | 8/1986 | Huppee | | 5,169,161 A | 12/1992 | Jones |
| 4,613,112 A | 9/1986 | Phlipot et al. | | D332,482 S | 1/1993 | Petty et al. |
| 4,616,859 A | 10/1986 | Brunet | | 5,176,406 A | 1/1993 | Straghan |
| 4,626,001 A | 12/1986 | Lee | | 5,178,303 A | 1/1993 | Blenkush et al. |
| 4,630,847 A | 12/1986 | Blenkush | | 5,181,752 A | 1/1993 | Benson et al. |
| 4,632,436 A | 12/1986 | Kimura | | D333,178 S | 2/1993 | Novy |
| 4,635,972 A | 1/1987 | Lyall | | 5,190,224 A | 3/1993 | Hamilton |
| 4,645,245 A | 2/1987 | Cunningham | | 5,222,279 A | 6/1993 | Frano et al. |
| 4,658,326 A | 4/1987 | Clark et al. | | 5,228,724 A | 7/1993 | Godeau |
| 4,659,116 A | 4/1987 | Cameron | | 5,232,020 A | 8/1993 | Mason et al. |
| 4,694,544 A | 9/1987 | Chapman | | D339,417 S | 9/1993 | Sampson et al. |
| 4,698,027 A | 10/1987 | Vandame | | 5,251,025 A | 10/1993 | Cooper et al. |
| 4,699,298 A | 10/1987 | Grant et al. | | 5,273,053 A | 12/1993 | Pohndorf |
| 4,700,926 A | 10/1987 | Hansen | | 5,297,826 A | 3/1994 | Percebois et al. |
| 4,703,957 A | 11/1987 | Blenkush | | 5,316,041 A | 5/1994 | Ramacier, Jr. et al. |
| 4,706,847 A | 11/1987 | Sankey et al. | | 5,318,332 A | 6/1994 | Hohmann et al. |
| 4,712,280 A | 12/1987 | Fildan | | 5,330,235 A | 7/1994 | Wagner et al. |
| 4,733,890 A | 3/1988 | Vyse | | 5,348,051 A | 9/1994 | Kallenbach |
| 4,738,401 A | 4/1988 | Filicicchia | | 5,348,354 A | 9/1994 | Badoureaux |
| 4,753,268 A | 6/1988 | Palau | | 5,353,836 A | 10/1994 | deCler et al. |
| 4,768,558 A | 9/1988 | Weber | | 5,356,183 A | 10/1994 | Cole |
| 4,776,067 A | 10/1988 | Sorensen | | 5,374,088 A | 12/1994 | Moretti et al. |
| 4,790,567 A | 12/1988 | Kawano et al. | | 5,385,311 A | 1/1995 | Morikawa et al. |
| 4,790,569 A | 12/1988 | Chaffee | | 5,385,331 A | 1/1995 | Allread et al. |
| 4,792,115 A | 12/1988 | Jindra et al. | | D357,307 S | 4/1995 | Ramacier, Jr. et al. |
| 4,793,637 A | 12/1988 | Laipply et al. | | 5,405,333 A | 4/1995 | Richmond |
| 4,806,123 A | 2/1989 | Konishi et al. | | 5,405,339 A | 4/1995 | Kohnen et al. |
| D300,361 S | 3/1989 | Tokarz | | 5,405,340 A | 4/1995 | Fageol et al. |
| 4,824,148 A | 4/1989 | Grabowski | | 5,411,300 A | 5/1995 | Mitsui |
| 4,827,921 A | 5/1989 | Rugheimer | | 5,417,442 A | 5/1995 | Jornhagen |
| 4,832,237 A | 5/1989 | Hurford, Jr. | | 5,421,622 A | 6/1995 | Godeau |
| 4,834,423 A | 5/1989 | DeLand | | 5,437,650 A | 8/1995 | Larkin et al. |
| 4,844,512 A | 7/1989 | Gahwiler | | 5,440,792 A | 8/1995 | Ida |
| 4,863,201 A | 9/1989 | Carstens | | 5,462,313 A | 10/1995 | Rea et al. |
| 4,863,202 A | 9/1989 | Oldford | | 5,494,074 A | 2/1996 | Ramacier, Jr. et al. |
| 4,896,402 A | 1/1990 | Jansen et al. | | D369,409 S | 4/1996 | Salter |
| 4,900,065 A | 2/1990 | Houck | | 5,507,733 A | 4/1996 | Larkin et al. |
| 4,903,995 A | 2/1990 | Blenkush et al. | | 5,511,527 A | 4/1996 | Lorraine et al. |
| 4,923,228 A | 5/1990 | Laipply et al. | | D372,093 S | 7/1996 | Sampson et al. |
| 4,928,859 A | 5/1990 | Krahn et al. | | 5,536,258 A | 7/1996 | Folden |
| 4,928,999 A | 5/1990 | Landriault et al. | | 5,542,712 A | 8/1996 | Klinger et al. |
| 4,934,655 A | 6/1990 | Blenkush et al. | | 5,547,166 A | 8/1996 | Engdahl |
| 4,935,992 A | 6/1990 | Due | | 5,547,230 A | 8/1996 | Bank et al. |
| 4,946,200 A | 8/1990 | Blenkush et al. | | 5,553,895 A | 9/1996 | Karl et al. |
| 4,946,204 A | 8/1990 | Boticki | | D375,160 S | 10/1996 | Sampson et al. |
| 4,949,745 A | 8/1990 | McKeon | | 5,568,946 A | 10/1996 | Jackowski |
| 4,966,398 A | 10/1990 | Peterson | | 5,595,217 A | 1/1997 | Gillen et al. |
| 4,969,879 A | 11/1990 | Lichte | | 5,601,317 A | 2/1997 | Crouse et al. |
| D313,067 S | 12/1990 | Kotake et al. | | 5,607,190 A | 3/1997 | Exandier et al. |
| D313,277 S | 12/1990 | Haining | | 5,617,609 A | 4/1997 | Bently |
| D314,050 S | 1/1991 | Sone | | 5,620,025 A | 4/1997 | Lewin |
| D314,233 S | 1/1991 | Medvick | | 5,628,726 A | 5/1997 | Cotter |
| 4,982,736 A | 1/1991 | Schneider | | D380,262 S | 6/1997 | Van Funderburk et al. |
| 4,991,880 A | 2/1991 | Bernart | | 5,639,064 A | 6/1997 | deCler et al. |
| 5,009,252 A | 4/1991 | Faughn | | D382,639 S | 8/1997 | Musgrave et al. |
| 5,015,014 A | 5/1991 | Sweeney | | D384,731 S | 10/1997 | Ramacier, Jr. et al. |

| | | | | | | |
|---|---|---|---|---|---|---|
| 5,681,062 | A | 10/1997 | Fukao et al. | 6,261,282 B1 | 7/2001 | Jepson et al. |
| 5,682,662 | A | 11/1997 | Coules et al. | 6,293,596 B1 | 9/2001 | Kinder |
| 5,683,117 | A | 11/1997 | Corbett et al. | 6,296,508 B1 | 10/2001 | Kuwahara et al. |
| D387,147 | S | 12/1997 | Vandermast et al. | 6,296,796 B1 | 10/2001 | Gordon |
| 5,692,783 | A | 12/1997 | Watanabe et al. | 6,302,147 B1 | 10/2001 | Rose et al. |
| 5,695,223 | A | 12/1997 | Boticki | 6,318,764 B1 | 11/2001 | Trede et al. |
| D388,876 | S | 1/1998 | Sampson | 6,344,033 B1 | 2/2002 | Jepson et al. |
| 5,709,244 | A | 1/1998 | Patriquin et al. | 6,382,593 B1 | 5/2002 | deCler et al. |
| 5,725,258 | A | 3/1998 | Kujawski | D459,206 S | 6/2002 | Caveney et al. |
| 5,737,810 | A | 4/1998 | Krauss | 6,402,207 B1 | 6/2002 | Segal et al. |
| 5,745,957 | A | 5/1998 | Khokhar et al. | 6,422,574 B1 | 7/2002 | Mooklar |
| 5,746,414 | A | 5/1998 | Weldon et al. | 6,423,053 B1 | 7/2002 | Lee |
| 5,762,646 | A | 6/1998 | Cotter | 6,439,620 B1 | 8/2002 | Guest |
| 5,784,750 | A | 7/1998 | Sankovic et al. | 6,454,314 B1 | 9/2002 | Grosspietsch et al. |
| 5,799,987 | A | 9/1998 | Sampson | 6,481,758 B1 | 11/2002 | Andre et al. |
| 5,820,614 | A | 10/1998 | Erskine et al. | 6,481,759 B1 | 11/2002 | Kawasaki et al. |
| 5,837,180 | A | 11/1998 | Linder et al. | 6,485,064 B1 | 11/2002 | Davidson |
| 5,845,943 | A | 12/1998 | Ramacier, Jr. et al. | 6,485,483 B1 | 11/2002 | Fujii |
| 5,855,568 | A | 1/1999 | Battiato et al. | 6,497,433 B1 | 12/2002 | Ketcham |
| 5,879,033 | A | 3/1999 | Hansel et al. | 6,505,866 B1 | 1/2003 | Nakamura et al. |
| 5,882,047 | A | 3/1999 | Ostrander et al. | 6,508,807 B1 | 1/2003 | Peters |
| 5,884,531 | A | 3/1999 | Koenig | 6,520,546 B2 | 2/2003 | Szabo |
| D407,803 | S | 4/1999 | Redman | D471,261 S | 3/2003 | Kozu |
| 5,897,142 | A | 4/1999 | Kulevsky | 6,540,263 B1 | 4/2003 | Sausner |
| 5,911,367 | A | 6/1999 | McInerney | 6,543,745 B1 | 4/2003 | Enerson |
| 5,911,403 | A | 6/1999 | deCler et al. | 6,595,964 B2 | 7/2003 | Finley et al. |
| 5,911,404 | A | 6/1999 | Cheng | 6,609,696 B2 | 8/2003 | Enerson |
| 5,930,424 | A | 7/1999 | Heimberger et al. | 6,612,634 B1 | 9/2003 | Zoppas |
| 5,937,501 | A | 8/1999 | Imgram | 6,626,419 B2 | 9/2003 | deCler et al. |
| 5,938,244 | A | 8/1999 | Meyer | 6,626,465 B2 | 9/2003 | Lacroix et al. |
| 5,941,577 | A | 8/1999 | Musellec | D481,125 S | 10/2003 | Hayamizu |
| 5,942,730 | A | 8/1999 | Schwarz et al. | 6,641,177 B1 | 11/2003 | Pinciaro |
| D413,967 | S | 9/1999 | Yuen | 6,649,829 B2 | 11/2003 | Garber et al. |
| 5,957,898 | A | 9/1999 | Jepson et al. | 6,652,007 B1 | 11/2003 | Hwang |
| 5,961,157 | A | 10/1999 | Baron et al. | D484,241 S | 12/2003 | Peters et al. |
| 5,964,485 | A | 10/1999 | Hame et al. | 6,669,681 B2 | 12/2003 | Jepson et al. |
| 5,965,077 | A | 10/1999 | Rowley et al. | 6,676,172 B2 | 1/2004 | Alksnis |
| 5,975,489 | A | 11/1999 | deCler et al. | D486,909 S | 2/2004 | Cise et al. |
| 5,984,378 | A | 11/1999 | Ostrander et al. | 6,688,654 B2 | 2/2004 | Romero |
| 5,988,704 | A | 11/1999 | Ryhman | 6,692,038 B2 | 2/2004 | Braun |
| 6,012,743 | A | 1/2000 | Godeau et al. | 6,695,817 B1 | 2/2004 | Fangrow |
| 6,015,171 | A | 1/2000 | Schorn | 6,705,591 B2 | 3/2004 | deCler |
| D419,861 | S | 2/2000 | Khokhar | 6,722,705 B2 | 4/2004 | Korkor |
| 6,019,348 | A | 2/2000 | Powell | 6,722,708 B2 | 4/2004 | Morohoshi et al. |
| 6,024,124 | A | 2/2000 | Braun et al. | 6,762,365 B2 | 7/2004 | Inoue et al. |
| 6,029,701 | A | 2/2000 | Chaffardon et al. | 6,767,017 B2 | 7/2004 | Crapart et al. |
| 6,032,691 | A | 3/2000 | Powell et al. | D495,050 S | 8/2004 | Guala |
| 6,041,805 | A | 3/2000 | Gydesen et al. | 6,783,520 B1 | 8/2004 | Candray et al. |
| D422,487 | S | 4/2000 | Khokhar | D497,428 S | 10/2004 | Hayamizu |
| 6,050,297 | A | 4/2000 | Ostrowski et al. | 6,799,747 B1 | 10/2004 | Lai |
| 6,076,234 | A | 6/2000 | Khokhar et al. | D498,533 S | 11/2004 | Hayamizu |
| 6,077,245 | A | 6/2000 | Heinrich et al. | 6,814,726 B1 | 11/2004 | Lauer |
| 6,077,259 | A | 6/2000 | Caizza et al. | 6,840,277 B1 | 1/2005 | Nimberger |
| 6,082,401 | A | 7/2000 | Braun et al. | 6,846,021 B2 | 1/2005 | Rohde et al. |
| 6,086,044 | A | 7/2000 | Guest | 6,848,602 B2 | 2/2005 | deCler et al. |
| 6,089,540 | A | 7/2000 | Heinrichs et al. | 6,848,723 B2 | 2/2005 | Lamich |
| 6,099,045 | A | 8/2000 | Pirona | 6,863,314 B2 | 3/2005 | Guest |
| 6,112,855 | A | 9/2000 | Camacho et al. | 6,871,669 B2 | 3/2005 | Meyer et al. |
| 6,123,690 | A | 9/2000 | Mejslov | 6,871,878 B2 | 3/2005 | Miros |
| 6,135,150 | A | 10/2000 | Powell et al. | D503,778 S | 4/2005 | Wicks |
| 6,135,992 | A | 10/2000 | Wang | 6,886,803 B2 | 5/2005 | Mikiya et al. |
| 6,142,538 | A | 11/2000 | Volgstadt et al. | 6,897,374 B2 | 5/2005 | Garber et al. |
| 6,145,896 | A | 11/2000 | Vitel et al. | 6,899,315 B2 | 5/2005 | Maiville et al. |
| 6,152,914 | A | 11/2000 | Van De Kerkhof et al. | 6,902,144 B2 | 6/2005 | deCler |
| 6,155,610 | A | 12/2000 | Godeau et al. | D507,647 S | 7/2005 | Beck et al. |
| 6,161,578 | A | 12/2000 | Braun et al. | 6,916,007 B2 | 7/2005 | deCler et al. |
| 6,176,523 | B1 | 1/2001 | Winslett | 6,916,050 B2 | 7/2005 | Milhas |
| 6,182,694 | B1 | 2/2001 | Sievers et al. | 6,926,311 B2 | 8/2005 | Chang et al. |
| 6,189,560 | B1 | 2/2001 | Reynolds | 6,929,246 B2 | 8/2005 | Arzenton et al. |
| 6,199,915 | B1 | 3/2001 | Becker | 6,945,273 B2 | 9/2005 | Reid |
| 6,199,919 | B1 | 3/2001 | Kawasaki et al. | 6,949,084 B2 | 9/2005 | Marggi et al. |
| 6,199,920 | B1 | 3/2001 | Neustadtl | 6,962,275 B2 | 11/2005 | deCler et al. |
| 6,206,028 | B1 | 3/2001 | Holden et al. | 6,978,800 B2 | 12/2005 | deCler et al. |
| 6,221,064 | B1 | 4/2001 | Nadal | 6,981,547 B2 | 1/2006 | Maguire et al. |
| 6,231,089 | B1 | 5/2001 | DeCler et al. | 6,997,486 B2 | 2/2006 | Milhas |
| D444,054 | S | 6/2001 | Bernard et al. | 6,997,919 B2 | 2/2006 | Olsen et al. |
| 6,250,688 | B1 | 6/2001 | Kirby | 7,005,581 B2 | 2/2006 | Burnette |
| 6,257,626 | B1 | 7/2001 | Campau | 7,011,342 B2 | 3/2006 | Guivarc'h et al. |
| 6,260,851 | B1 | 7/2001 | Baron | 7,014,214 B2 | 3/2006 | Kaneko |

| | | |
|---|---|---|
| D522,109 S | 5/2006 | White et al. |
| 7,040,670 B2 | 5/2006 | Madden |
| 7,044,161 B2 | 5/2006 | Tiberghien |
| 7,044,506 B2 | 5/2006 | Dong |
| D523,553 S | 6/2006 | Beck et al. |
| 7,080,665 B2 | 7/2006 | Whall |
| 7,081,223 B2 | 7/2006 | Khoury |
| 7,108,297 B2 | 9/2006 | Takayanagi et al. |
| 7,118,138 B1 | 10/2006 | Rowley et al. |
| 7,128,348 B2 | 10/2006 | Kawamura et al. |
| 7,137,654 B2 | 11/2006 | Segal et al. |
| 7,140,592 B2 | 11/2006 | Phillips |
| 7,147,252 B2 | 12/2006 | Teuscher et al. |
| 7,150,478 B2 | 12/2006 | Poirier et al. |
| 7,153,296 B2 | 12/2006 | Mitchell |
| 7,163,022 B2 | 1/2007 | Whall |
| D540,944 S | 4/2007 | Guala |
| 7,210,917 B2 | 5/2007 | Lai et al. |
| D547,446 S | 7/2007 | Racz et al. |
| D550,355 S | 9/2007 | Racz et al. |
| D557,409 S | 12/2007 | Veliss et al. |
| 7,316,428 B2 | 1/2008 | Takayanagi et al. |
| D564,660 S | 3/2008 | Hayashi |
| 7,343,931 B2 | 3/2008 | Packham |
| D567,340 S | 4/2008 | Tiberghien |
| 7,352,771 B2 | 4/2008 | Garber |
| D569,507 S | 5/2008 | Blanchard |
| D569,955 S | 5/2008 | Chen |
| 7,377,553 B2 | 5/2008 | Takayanagi |
| D570,457 S | 6/2008 | Brown |
| 7,390,029 B2 | 6/2008 | Matsubara |
| 7,394,375 B2 | 7/2008 | Johnson |
| 7,434,842 B2 | 10/2008 | Schmidt |
| 7,434,846 B2 | 10/2008 | Baumgartner |
| 7,448,653 B2 | 11/2008 | Jensen et al. |
| 7,464,970 B2 | 12/2008 | Yamada et al. |
| 7,467,813 B2 | 12/2008 | Gunderson |
| 7,469,472 B2 | 12/2008 | DeCler et al. |
| 7,478,840 B2 | 1/2009 | Youssefifar |
| 7,488,446 B2 | 2/2009 | Meyer et al. |
| 7,494,156 B2 | 2/2009 | Okada |
| 7,503,595 B2 | 3/2009 | McKay |
| 7,516,990 B2 | 4/2009 | Jamison et al. |
| 7,546,857 B2 | 6/2009 | Chadbourne et al. |
| 7,547,047 B2 | 6/2009 | deCler et al. |
| D595,845 S | 7/2009 | Miros et al. |
| D595,846 S | 7/2009 | Racz et al. |
| D596,288 S | 7/2009 | Racz et al. |
| D596,739 S | 7/2009 | Ng et al. |
| 7,562,906 B2 | 7/2009 | Schmidt |
| 7,566,077 B2 | 7/2009 | Tsurumi |
| 7,581,763 B2 | 9/2009 | Salomon-Bahls |
| D602,128 S | 10/2009 | Williams et al. |
| 7,614,666 B2 | 11/2009 | Eggert et al. |
| 7,631,660 B2 | 12/2009 | deCler et al. |
| 7,647,954 B2 | 1/2010 | Garber et al. |
| 7,666,178 B2 | 2/2010 | McMichael |
| D612,019 S | 3/2010 | Williams et al. |
| D612,021 S | 3/2010 | Schmidt |
| 7,677,608 B2 | 3/2010 | Takayanagi |
| D613,853 S | 4/2010 | Ng et al. |
| 7,695,020 B2 | 4/2010 | Schmidt |
| 7,708,025 B2 | 5/2010 | Johnson |
| 7,731,244 B2 | 6/2010 | Miros et al. |
| D619,706 S | 7/2010 | Schon et al. |
| 7,770,939 B2 | 8/2010 | Jensen et al. |
| 7,806,139 B2 | 9/2010 | Packham et al. |
| 7,841,357 B2 | 11/2010 | Rankin |
| D629,894 S | 12/2010 | Lombardi, III et al. |
| 7,849,877 B2 | 12/2010 | Tan et al. |
| D630,320 S | 1/2011 | Lombardi, III et al. |
| D632,783 S | 2/2011 | Maesarapu |
| 7,878,553 B2 | 2/2011 | Wicks et al. |
| D634,840 S | 3/2011 | Lombardi, III et al. |
| D639,398 S | 6/2011 | Wilhelm |
| 7,954,374 B2 | 6/2011 | Rankin |
| 7,954,515 B2 | 6/2011 | Gerst |
| D642,244 S | 7/2011 | Wilhelm |
| 7,976,071 B2 | 7/2011 | Bibby |
| D645,547 S | 9/2011 | Lombardi, III et al. |
| D649,240 S | 11/2011 | Lewis et al. |
| D650,478 S | 12/2011 | Lewis |
| D652,510 S | 1/2012 | Lombardi, III et al. |
| D652,511 S | 1/2012 | Lombardi, III et al. |
| D654,573 S | 2/2012 | Lombardi, III et al. |
| 8,113,546 B2 | 2/2012 | Jensen et al. |
| D655,393 S | 3/2012 | Whitaker |
| D663,022 S | 7/2012 | Lombardi, III et al. |
| 8,235,426 B2 * | 8/2012 | Pisula et al. .................. 285/308 |
| 2002/0022762 A1 | 2/2002 | Beane et al. |
| 2002/0070547 A1 | 6/2002 | Guertin |
| 2002/0093192 A1 | 7/2002 | Matkovich |
| 2002/0140172 A1 | 10/2002 | Platusich |
| 2002/0156344 A1 | 10/2002 | Pasricha et al. |
| 2002/0185861 A1 | 12/2002 | Inoue |
| 2003/0004397 A1 | 1/2003 | Kameya et al. |
| 2003/0067162 A1 | 4/2003 | Welsh et al. |
| 2003/0193188 A1 | 10/2003 | Miros |
| 2003/0230894 A1 | 12/2003 | Cleveland et al. |
| 2004/0021318 A1 | 2/2004 | Fritze et al. |
| 2004/0056484 A1 | 3/2004 | Kwon et al. |
| 2004/0094903 A1 | 5/2004 | Sutherland |
| 2004/0195830 A1 | 10/2004 | Gilmour |
| 2004/0199143 A1 | 10/2004 | Lauer |
| 2004/0227346 A1 | 11/2004 | Jamison et al. |
| 2004/0232696 A1 | 11/2004 | Andre |
| 2005/0033237 A1 | 2/2005 | Fentress et al. |
| 2005/0046184 A1 | 3/2005 | Chang |
| 2005/0057042 A1 | 3/2005 | Wicks |
| 2005/0082828 A1 | 4/2005 | Wicks et al. |
| 2005/0087981 A1 | 4/2005 | Yamada et al. |
| 2005/0209583 A1 | 9/2005 | Powers et al. |
| 2005/0217265 A1 | 10/2005 | Popp et al. |
| 2005/0242579 A1 | 11/2005 | Bright et al. |
| 2005/0275220 A1 | 12/2005 | Shu |
| 2006/0066100 A1 | 3/2006 | Nakashima et al. |
| 2006/0152003 A1 | 7/2006 | Slunick et al. |
| 2006/0202146 A1 | 9/2006 | Doyle |
| 2006/0264814 A1 | 11/2006 | Sage |
| 2006/0293629 A1 | 12/2006 | Cote, Sr. et al. |
| 2007/0025811 A1 | 2/2007 | Wilhelm |
| 2007/0029795 A1 | 2/2007 | Moner et al. |
| 2007/0029796 A1 | 2/2007 | Bibby |
| 2007/0106213 A1 | 5/2007 | Spera et al. |
| 2007/0137718 A1 | 6/2007 | Rushlander et al. |
| 2007/0209716 A1 | 9/2007 | Rankin |
| 2007/0284875 A1 | 12/2007 | Salomon-Bahls et al. |
| 2008/0007051 A1 | 1/2008 | Jensen et al. |
| 2008/0011703 A1 | 1/2008 | Schmeisser et al. |
| 2008/0012314 A1 | 1/2008 | Harger et al. |
| 2008/0018105 A1 | 1/2008 | Le Bars |
| 2008/0048448 A1 | 2/2008 | Jamison et al. |
| 2008/0078464 A1 | 4/2008 | Loewe |
| 2008/0111371 A1 | 5/2008 | Feger et al. |
| 2008/0111372 A1 | 5/2008 | Trede et al. |
| 2008/0129047 A1 | 6/2008 | Blivet et al. |
| 2008/0164694 A1 | 7/2008 | Zdroik et al. |
| 2008/0191466 A1 | 8/2008 | Knipple et al. |
| 2008/0200901 A1 | 8/2008 | Rasmussen et al. |
| 2008/0277923 A1 | 11/2008 | Brandt et al. |
| 2008/0277924 A1 | 11/2008 | Jensen et al. |
| 2008/0284167 A1 | 11/2008 | Lim et al. |
| 2008/0287920 A1 | 11/2008 | Fangrow et al. |
| 2009/0079187 A1 | 3/2009 | Malone |
| 2009/0127847 A1 | 5/2009 | Hagen et al. |
| 2009/0129047 A1 | 5/2009 | Park et al. |
| 2009/0140519 A1 | 6/2009 | Pavnaskar et al. |
| 2009/0167018 A1 | 7/2009 | Lien |
| 2009/0187166 A1 | 7/2009 | Young |
| 2009/0188575 A1 | 7/2009 | Williams et al. |
| 2010/0001516 A1 | 1/2010 | Pisula, Jr. et al. |
| 2010/0056975 A1 | 3/2010 | Dale et al. |
| 2010/0078934 A1 | 4/2010 | Matsunaga |
| 2010/0185040 A1 | 7/2010 | Uber et al. |
| 2010/0194100 A1 | 8/2010 | Koch |
| 2010/0276922 A1 | 11/2010 | Rehder et al. |
| 2010/0295295 A1 | 11/2010 | Schmidt |
| 2010/0301599 A1 | 12/2010 | Jensen et al. |

| | | | |
|---|---|---|---|
| 2010/0319796 A1 | 12/2010 | Whitaker | |
| 2011/0012340 A1 | 1/2011 | Packham et al. | |
| 2011/0127767 A1 | 6/2011 | Wicks et al. | |
| 2011/0204621 A1 | 8/2011 | Whitaker et al. | |
| 2011/0204622 A1 | 8/2011 | Lewis et al. | |
| 2011/0210541 A1 | 9/2011 | Lewis et al. | |
| 2012/0031515 A1 | 2/2012 | Whitaker | |
| 2012/0068457 A1 | 3/2012 | Pisula, Jr. et al. | |
| 2012/0299296 A1 | 11/2012 | Lombardi, III | |

FOREIGN PATENT DOCUMENTS

| | | |
|---|---|---|
| DE | 3439522 | 8/1985 |
| DE | 3533000 | 3/1987 |
| DE | 4122455 | 1/1993 |
| DE | 19800050 | 7/1998 |
| DE | 102005015343 | 10/2006 |
| EP | 0360634 | 3/1990 |
| EP | 0390746 | 10/1990 |
| EP | 0267067 | 7/1991 |
| EP | 0482277 | 4/1992 |
| EP | 0592823 | 4/1994 |
| EP | 0715111 | 6/1996 |
| EP | 0865779 | 9/1998 |
| EP | 0877891 | 11/1998 |
| EP | 0890054 | 1/1999 |
| EP | 0982525 | 3/2000 |
| EP | 1497582 | 1/2005 |
| EP | 1564469 | 8/2005 |
| EP | 1843074 | 10/2007 |
| FR | 2031965 | 11/1970 |
| FR | 2429370 | 1/1980 |
| FR | 280871 | 10/2001 |
| FR | 2853043 | 10/2004 |
| FR | 2870921 | 12/2005 |
| FR | 2903164 | 1/2008 |
| GB | 583459 | 12/1946 |
| GB | 890775 | 3/1962 |
| GB | 2177769 | 1/1987 |
| GB | 2218166 | 11/1989 |
| GB | 2271157 | 4/1994 |
| GB | 2379253 | 3/2003 |
| JP | 53-006918 | 1/1978 |
| JP | 5-223189 | 8/1993 |
| JP | 7-145889 | 6/1995 |
| JP | 10-169869 | 6/1998 |
| JP | 11-82849 | 3/1999 |
| JP | 2003-42363 | 2/2003 |
| JP | 2003-42368 | 2/2003 |
| JP | 6-512540 | 4/2006 |
| WO | WO 93/17270 | 9/1993 |
| WO | WO 95/08732 | 3/1995 |
| WO | WO 00/79172 | 12/2000 |
| WO | WO 2004/027269 | 4/2004 |
| WO | WO 2004/104466 | 12/2004 |
| WO | WO 2005/064216 | 7/2005 |
| WO | WO 2006/031958 | 3/2006 |
| WO | WO 2006/073778 | 7/2006 |
| WO | WO 2006/084171 | 8/2006 |
| WO | WO 2006/135666 | 12/2006 |
| WO | WO 2007/038222 | 4/2007 |
| WO | WO 2007/116387 | 10/2007 |
| WO | WO 2007/120620 | 10/2007 |
| WO | WO 2008/023021 | 2/2008 |
| WO | WO 2009/026441 | 2/2009 |

OTHER PUBLICATIONS

Barbed Tee Adapter, ½ in to ⅜ in to ½ in [Item # F1728], http://www.horticulturesource.com/product_info.php/products_id/4016/language/en; dated accessed Sep. 14, 2009, 3 pages.

Brochure, "Precision Components", Value Plastics, Inc., 2002, Feb. 2002, 132 pages.

Capabilities [online], Jay Manufacturing Corp., retrieved on Apr. 9, 2010, retrieved from the Internet: <URL: http://www.jaymfg.com/capabilities.htm>, 2 pages.

Flojet "Quick Connect" Port System Adapter 90 Elbow Type Quad Port X ½" Hose Barb, http://www.amazon.com/Quick-Connect-Port-System-Quad-Barb-90/dp/B0000AZ771/ref=sr_1_16?s=sporting-goods&ie=UTF8&qid=1300220596&sr=1-16, date accessed Sep. 14, 2009; 3 pages.

High-Flow Quick Disconnect Couplings; http://www.coleparmer.com/catalog/product_view.asp?sku=3130355; date accessed Sep. 14, 2009, 3 pages.

Mills, The Process of Vacuum-forming Plastic Parts, IPFrontline.com [online], retrieved on Apr. 9, 2010, retrieved from the Internet: <URL: http://www.ipfrontline.com/depts/article.asp?id=453&deptid=2>, 3 pages.

Nylon, Polypropylene Kynar (PVDF) Plastic Fittings for Flexible Tubing & Hose, http://www.omega.com/pdf/tubing/fittings—tubing_hose/nylon_poly_kynar/nylon.asp; dated accessed Sep. 14, 2009, 2 pages.

Science of Hose Barbs, Colder Products Company, http://www.pddnet.com/article-the-science-of-hose-barbs/, date accessed Sep. 4, 2009, 6 pages.

Stackable Hose Barb Elbow—½" CTSx½ ID Barb, http://www.freshwatersystems.com/p-1714-stackable-hose-barb-elbow-12-cts-x-12-id-barb.aspx?affiliatied=10052&utm_source=shopzilla&utm_medium=Feed&utm_campaign=Product&utm_term=3512-1008, date accessed Sep. 14, 2009, 1 page.

Stainless Steel Overview: History [online], Stainless Steel Industry of North America, retrieved on Apr. 9, 2010, retrieved from the Internet: <URL: http://www.ssina.com/overview/history.html>, 1 page.

Office Action dated Aug. 31, 2010, U.S. Appl. No. 12/167,833, 12 pages.

Amendment dated Dec. 31, 2010, U.S. Appl. No. 12/167,833, 10 pages.

Office Action dated Mar. 9, 2011, U.S. Appl. No. 12/167,833, 11 pages.

Amendment dated Sep. 9, 2011, U.S. Appl. No. 12/167,833, 12 pages.

Final Office Action dated Nov. 4, 2011, U.S. Appl. No. 12/167,833, 7 pages.

Amendment dated Mar. 5, 2012, U.S. Appl. No. 12/167,833, 11 pages.

Notice of Allowance and Fee(s) Due dated Apr. 3, 2012, U.S. Appl. No. 12/167,833, 8 pages.

Office Action dated Nov. 21, 2012, U.S. Appl. No. 13/265,191, 13 pages.

* cited by examiner

LATCH ASSEMBLY FOR JOINING TWO CONDUITS

CROSS REFERENCE TO RELATED APPLICATION

This application is a continuation of U.S. patent application Ser. No. 12/167,833, entitled "Latch Assembly for Joining Two Conduits," filed on Jul. 3, 2008, now U.S. Pat. No. 8,235,426, which is hereby incorporated herein by reference.

FIELD OF TECHNOLOGY

The present invention relates to a coupling device. More particularly, the present invention relates to a coupling device for conduits. Even more particularly, the present invention relates to a releasably latching coupling device for fluid conduits.

BACKGROUND

The use of conduits is well known for transporting fluids in the form of liquids or gases to and from various locations. Conduits can also be used for transporting solids of various forms. It is also well known that splices are often necessary within a given length of conduit for extending the length of the conduit, providing for redirection of a conduit, providing connections to supply reservoirs or distribution devices, or other known reasons.

In light of the many uses of conduits and the known need for splicing conduits, several devices exist for assisting the splicing of a conduit. For example, a garden hose splice involves a threaded male end and a threaded female end that may be used to splice more than one garden hose together. A similar connection may be used at the connection of the hose to a water spout at one end and to a water distribution device such as a sprinkler or nozzle at the other end. As an additional example, rubber tubing may often be spliced or connected to equipment through the use of a hose barb.

In the medical industry, conduits are often used to transport fluids in the form of liquids or gases from reservoirs to patients, from reservoirs to equipment, between equipment, or otherwise. Also, splices in these conduits are frequently connected, unconnected, and rearranged as patients are transported, equipment is moved, and procedures are conducted. Existing threaded connections often require attention to assure the threads are aligned and can also be time consuming to screw together. Practitioners need to be efficient and sometimes need to act quickly in an emergency. Thus, these connections need to be made in a simple motion and in a timely fashion. Patient safety requires that these connections remain secure in an environment where the conduit may be pulled on, tripped over, or otherwise treated so as to inadvertently undue a splice or a connection. Finally, patient safety also requires that the connection provides for uninterrupted flow of the transported material through the connection.

The information included in this Background section of the specification, including any references cited herein and any description or discussion thereof, is included for technical reference purposes only and is not to be regarded subject matter by which the scope of the invention as defined in the claims is to be bound.

SUMMARY

In one embodiment, a connector assembly is provided for coupling together first and second fluid conduits. The assembly includes a first connector with a proximal end for coupling with the first fluid conduit, a distal end opposite the proximal end, a fluid pathway between the proximal and distal ends, and a housing extending about at least a portion of the fluid pathway. The housing of the first connector includes a slot and a cantilevered release button extending distally to a free end of the button from a fixed end of the button. The assembly also includes a second connector including a proximal end for coupling with the second fluid conduit, a distal end opposite the proximal end, a fluid pathway between the proximal and distal ends, and a housing extending about at least a portion of the fluid pathway. The housing of the second connector includes a cantilevered region extending proximally to a free end of the cantilevered region from a fixed end of the cantilevered region with an engagement feature at its proximal end. When the distal ends of the described first and second connectors are moved towards each other in opposed fashion, the cantilevered region together with the engagement feature pass underneath the slot to engage the slot and connect the first connector to the second connector.

In another embodiment, a connector assembly for coupling together first and second fluid conduits is provided. The assembly includes a first connector including a proximal end for coupling with the first fluid conduit, a distal end opposite the proximal end, a fluid pathway between the proximal and distal ends, and a housing extending about at least a portion of the fluid pathway. The housing of the first connector includes a cantilevered button extending proximally to a free end of the button from a fixed end of the button. The assembly also includes a second connector including a proximal end for coupling with the second fluid conduit, a distal end opposite the proximal end, a fluid pathway between the proximal and distal ends, and a housing extending about at least a portion of the fluid pathway. The housing of the second connector includes a connection opening. When the distal ends of the first and second connectors are moved towards each other in opposed fashion, the cantilevered button passes underneath the connection opening to be received in the connection opening, engage the connection opening, and connect the first connector to the second connector.

In another embodiment, a latch assembly for connection of conduit is provided, including a female portion with a shell, a slot, and a release button. The latch assembly also includes a male portion with a shell and a cantilevered region with an engagement feature. The cantilevered region is adapted to deflect upon engagement with the female portion. The engagement feature is adapted to engage the slot thus releasing the deflection of the cantilevered region. The release button is adapted to disengage the engagement feature from the slot when depressed allowing separation of the female and male portions.

In a further embodiment, a latch assembly for connection of conduit is provided, including a female portion with a shell and a connection opening. The latch assembly also includes a male portion with a shell and a cantilevered release button. The cantilevered release button is adapted to deflect upon engagement with the female portion and further engage the connection opening releasing the deflection. The cantilevered release button is also adapted to disengage the connection opening when depressed allowing separation of the female and male portions.

In yet another embodiment, a connector assembly for coupling together first and second fluid conduits is provided. The assembly includes a first connector and a second connector. The first connector includes a proximal end for coupling with the first fluid conduit, a distal end opposite the proximal end, a fluid pathway between the proximal and distal ends, and a housing extending about at least a portion of the fluid pathway. The housing includes a slot and a cantilevered release button extending distally to a free end of the button from a fixed end of the button. The second connector includes a proximal end for coupling with the second fluid conduit, a distal end opposite the proximal end, a fluid pathway between the proximal and distal ends, and a housing extending about at least a portion of the fluid pathway. The housing includes a cantilevered region extending distally to a free end of the cantilevered region from a fixed end of the cantilevered region with an engagement feature near the free end of the cantilevered region. When the distal ends of the connectors are moved towards each other in opposed fashion, the cantilevered region passes underneath the slot to allow the engagement feature to engage the slot and connect the first connector to the second connector.

In another implementation, a connector assembly for coupling together first and second fluid conduits is composed of a first connector and a second connector. The first connector has a proximal end for coupling with the first fluid conduit, a distal end opposite the proximal end, a fluid pathway between the proximal and distal ends, and a first housing extending about at least a portion of the fluid pathway. The first housing may have opposing major faces and peripheral sidewalls connecting the major faces. The first housing may also define a slot in each of the major faces open to an inner cavity within the first housing that at least partially defines a respective cantilevered release button within each of the major faces of the first housing extending distally to a free end of the cantilevered release button from a fixed end of the cantilevered release button. The second connector may have a proximal end for coupling with the second fluid conduit, a distal end opposite the proximal end, a fluid pathway between the proximal and distal ends, and a second housing extending about at least a portion of the fluid pathway. The second housing may have opposing major walls each defining a cantilevered region therein extending proximally to a free end of the cantilevered region from a fixed end of the cantilevered region with an engagement feature near the free end of the cantilevered region. When the distal ends of the connectors are moved towards each other in opposed fashion, the cantilevered regions pass underneath the slots to allow the engagement features to engage the slots and connect the first connector to the second connector.

In a further implementation, a latch assembly for the connection of conduits, the latch assembly is composed of a first connector and a second connector. The first connector may have a first housing, a slot defined within a wall of the housing such that the slot is open to an inner cavity within the first housing, and a release button forming a part of the wall of the first housing and defined at least partially by the slot. The second connector may have a second housing that defines a cantilevered region within a wall of the second housing, the cantilevered region further having an engagement feature. The cantilevered region may be adapted to engage with the first housing of the first connector without deflecting the release button. The engagement feature may be adapted to engage the slot. The release button may be adapted to disengage the engagement feature from the slot when depressed, thereby allowing separation of the female and male portions.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

DETAILED DESCRIPTION

The accompanying drawings, descriptive material and this description depict and describe embodiments of a latch assembly for joining two fluid conduits together. The conduits may be tubing for carrying gas or liquid to and from patients or equipment in the medical industry, but may also be any type of conduit in any industry. The assembly may include a male portion and a female portion which form a mating connection. The male or female portion may be attached to an end of a conduit and used to connect to a male or female portion attached to the end of another conduit or device. The male and female portions may provide a latching connection that engages as the two portions are advanced toward each other and may be released using a pressing motion. The connection between the male and female portions of the assembly may create an associated connection between the associated conduits or devices. The assembly may provide for efficient, secure, and effective coupling of conduits.

With regard to fastening, mounting, attaching or connecting components of the present invention, unless specifically described otherwise, such are intended to encompass conventional fasteners such as dowels, ties, bolts, screws, rivets, pins, and the like. Components may also be connected by welding, fusing, pressing, or melting, if appropriate, and appropriate liquid and/or water tight seals or sealing devices may be used. Unless specifically otherwise disclosed or taught, materials for making the present invention and/or components thereof may be selected from appropriate materials such as plastics, metals, composite materials and the like, and appropriate manufacturing or production methods including those known to ones skilled in the art may be used.

The present invention may be more completely understood with reference to the Figures, which are described below.

Figure 1:
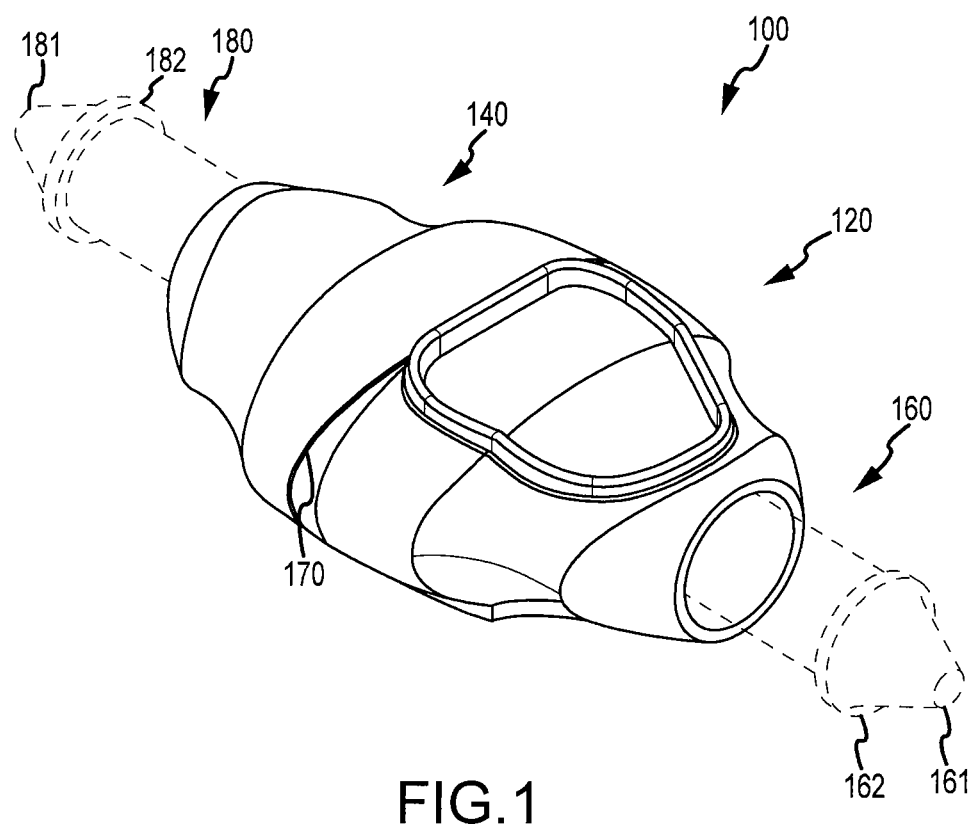
FIG. 1 is an isometric view of a latch assembly according to certain embodiments.
Figure 2:
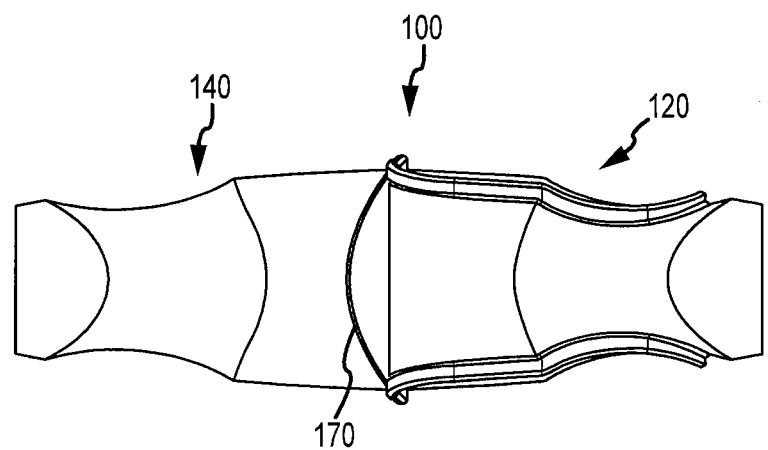
FIG. 2 is a left view of a latch assembly according to certain embodiments.

FIGS. 1-4 show a latch assembly 100 according to certain embodiments. In one embodiment, the latch assembly includes a female portion 120 and a male portion 140, which latch together forming a seam 170. Shown in phantom on FIG. 1 are two conduits 160 and 180 associated with the female portion 120 and male portion 140 respectively. The conduits shown include a proximal end 161, 181 with a hose barb 162, 182. While in one embodiment, hose barbs 162, 182 may be provided for joining the proximal ends 161, 181 to polymer tubing, in other embodiments, the proximal ends 161, 181 may be provided with other joining features, such as threads, flanges, couplings, clamps, etc.

Referring to FIG. 3, the conduits are again shown in phantom and each have a distal end 163, 183. The conduits are shown in mating relationship where the distal end 163 associated with the female portion 120 is a female distal end and the distal end 183 associated with the male portion 140 is a male distal end. Those skilled in the art will understand and appreciate that the distal end 163 could instead be a male distal end and the distal end 183 could instead be a female distal end.

The remaining disclosure relates to several embodiments of the latch assembly and does not discuss the conduit specifically. It is intended that each of the embodiments may include a conduit associated with the male portion of the latch assembly and a conduit associated with a female portion of the latch assembly. The connection between the two conduits, apart from the latch assembly connection, may be a male/female connection as discussed above, a flanged connection or some other type of abutting connection, or any type of conduit connection known in the art. In addition, a gasket or other sealing means known in the art may be incorporated at the conduit connection to prevent leaking or other escape of matter from the conduits at the connection.

The present disclosure is intended to include any type of conduit including, but not limited to, tubing, piping, ducting, or other canal type devices for use in transporting matter.

It is further intended that the conduit may be connected to or otherwise restrained by the associated portion of the latch assembly in some form. The relationship between the conduit and the latch assembly may be a fixed connection, a sleeved connection, or any other connection known in the art. Additionally, the conduit may be a molded portion of the assembly. Finally, features of the latch assembly may include devices or structures associated with assisting the connection of the included conduits. For example, opposing annular rings may be included on each male/female portion of the latch assembly for passing through of a flanged conduit, such that, when assembled, the opposing annular rings on each portion of the assembly would compress the respective flanges of the conduit together providing a sealing force. Other devices or structures for assisting with the conduit connection and sealing known in the art are also included.

FIGS. 5-8 show the female portion 120 of the embodiment shown in FIGS. 1-4 in greater detail. In this embodiment, the female portion 120 of the latch assembly 100 is shown to have a proximal end 121 and a distal end 122. The female portion 120 is also shown to include a shell 125 and a connection assembly 135.

In the present embodiment, the shell 125 of the female portion 120 has a longitudinal axis 123. The shell 125 is generally hollow with a varying oblong shaped cross-section when viewed along the longitudinal axis 123. The cross-section varies from relatively narrow at its proximal end 121 to relatively broad at its distal end 122. The shell 125 includes an exit opening/connection for a conduit at the proximal end 121. The shell 125 further includes an abutment face 129 at the distal end 122, the abutment face 129 following the perimeter contour of the shell 125. Those skilled in the art will understand and appreciate that virtually any shaped cross-section may be used including, but not limited to, circular, square, and rectangular shapes.

Figure 7:
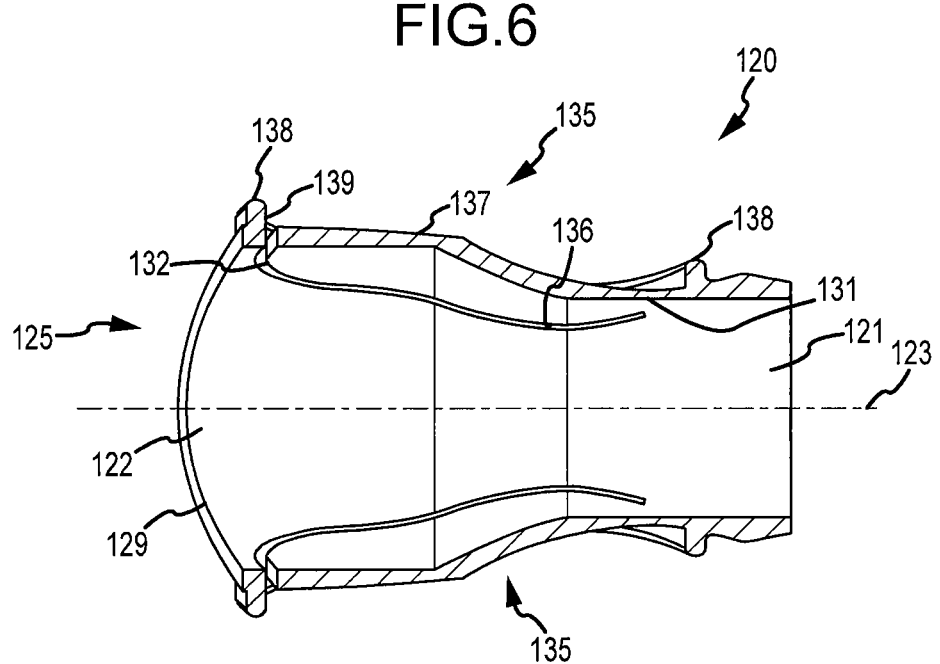
FIG. 7 is a left section view of a female portion of a latch assembly according to certain embodiments.
Figure 8:
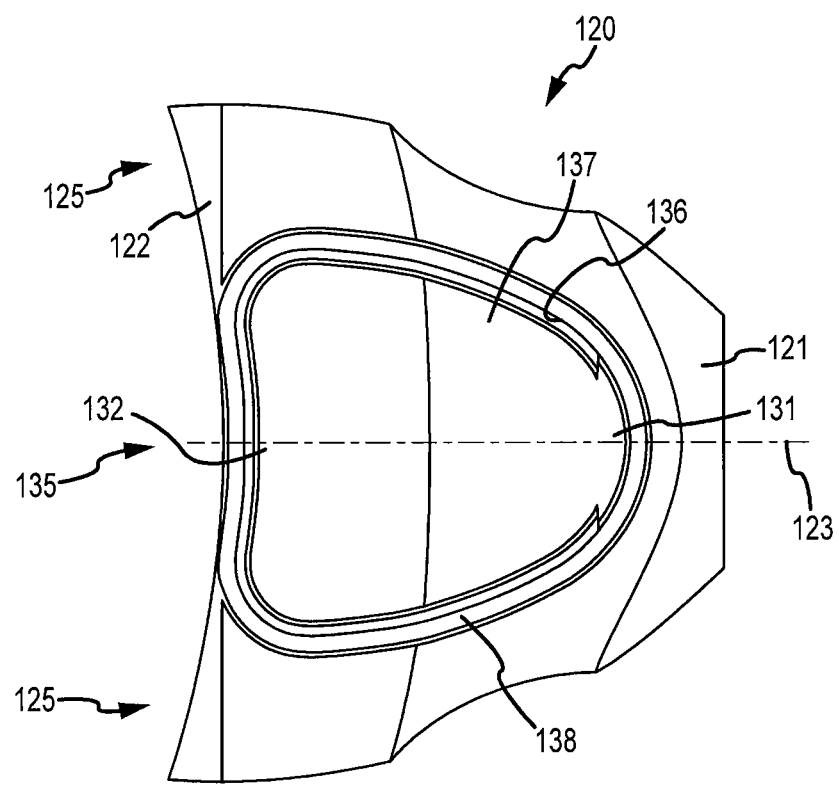
FIG. 8 is a top view of a female portion of a latch assembly according to certain embodiments.
Figure 9:
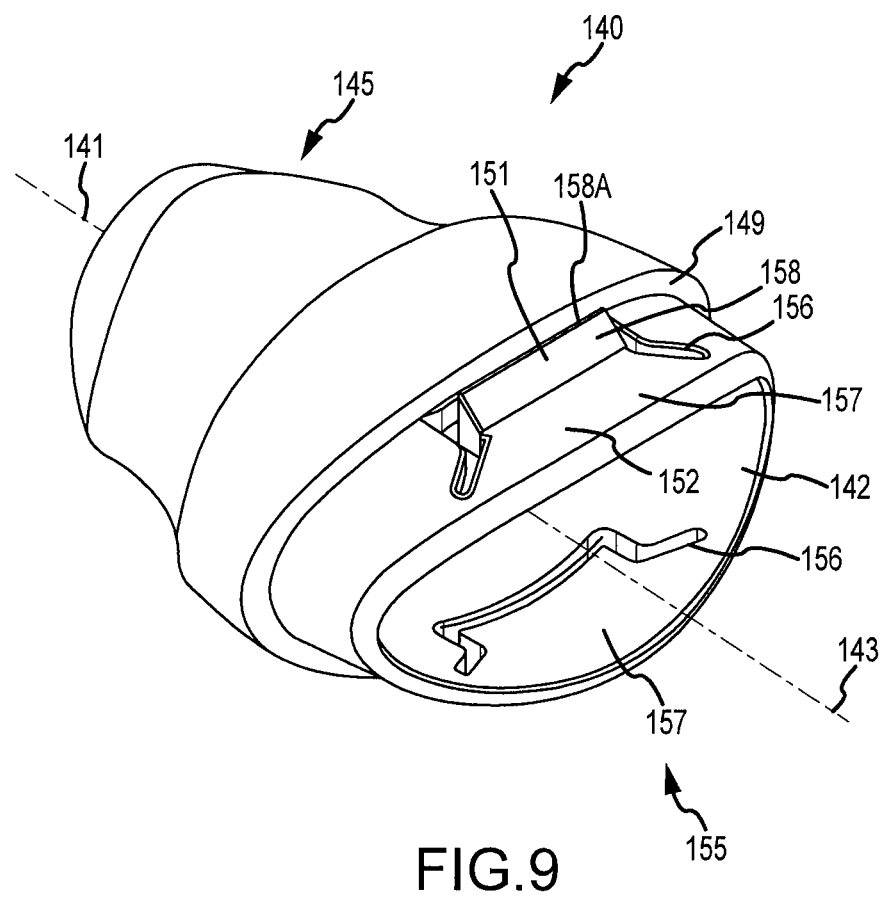
FIG. 9 is an isometric view of a male portion of a latch assembly according to certain embodiments.

In the present embodiment, the connection assembly 135 of the female portion 120, as best shown in FIGS. 7 and 8, comprises a release button 137, a molded-in slot 136, and a raised rib 138. It is noted that the female portion 120 includes two connection assemblies 135 located on opposing surfaces of the female portion 120. For purpose of description, only one of the connection assemblies 135 is described herein.

In this embodiment, the release button 137 comprises a section of the shell 125 and thus matches the contour of the shell 125, but is separated from the shell 125 by a molded-in slot 136 and a raise rib 138. The release button further has a proximal end 131 and a distal end 132, where the proximal end 131 is near the proximal end 121 of the female portion 120 and the distal end 132 is near the distal end 122 of the female portion 120.

In this embodiment, the release button 137 is surrounded by the molded-in slot 136 on three sides and part of a fourth side. Regarding the first three sides, two are generally parallel to the longitudinal axis 123 and the third side is along the release button's distal end 132. The fourth side, where the molded-in slot 136 only partially surrounds the release button 137, is along the release button's proximal end 131. The molded-in slot 136 creates a peninsula-like shaped release button 137 in a cantilevered condition where the release button 137 increases in width as it extends from the proximal end 131 to the distal end 132. The cantilevered condition allows the distal end 132 of the release button 137 to flex into the interior space of the female portion 120 when pressed on from the outer side.

In contrast to the molded-in slot 136, the raised rib 138 is shown to completely surround the release button 137. The raised rib 138 projects outwardly relative to the inner space of the female portion 120 and has a side face 139 defining the outer perimeter of the molded-in slot 136.

FIGS. 9-12 show the male portion 140 of the embodiment shown in FIGS. 1-4 in greater detail. The male portion 140 of the latch assembly 100 is shown to have a proximal end 141 and a distal end 142. The male portion 140 is also shown to include a shell 145 and a connection assembly 155.

In the present embodiment, the shell 145 has a longitudinal axis 143. The shell 145 is generally hollow with a varying oblong shaped cross-section when viewed along the longitudinal axis 143. The outer contour of the shell 145 at its distal end matches the outer contour of the shell 125 at its distal end 122. This provides for a smooth surface transition between the female 120 and male 140 portions of the latch assembly 100. The cross-section of the shell 145 varies from relatively narrow at its proximal end 141 to relatively broad at its distal end and includes an opening/connection for a conduit at its proximal end 141. Those skilled in the art will understand and appreciate that virtually any shaped cross-section can be used including, but not limited to circular, square, and rectangular shapes. Those skilled in the art will also understand and appreciate that a smooth transition may not always be necessary or desired and thus the outer contour of the shell 125 and the shell 145 would not need to match.

In the present embodiment, the connection assembly 155 of the male portion 140 is situated at the distal end 142 of the male portion 140 and is separated from the shell 145 by an abutment face 149. The connection assembly 155 comprises a necked-down section of the shell 145. The outer contour of the connection assembly 155 substantially matches the inner contour of the shell 125 of the female portion 120 at its distal end 122. This provides for a mating relationship between the female portion 120 and the male portion 140 where the connection assembly 155 extends within the shell 125.

In this embodiment, the connection assembly 155 further comprises a cantilevered region 157, a molded-in slot 156, and a ramped engagement feature 158. It is noted that the connection assembly 155 includes two cantilevered regions 157 located on opposing surfaces of the connection assembly 155. For purposes of description, only one of the cantilevered regions 157 is described herein.

In the present embodiment, the cantilevered region 157 is a section of the connection assembly 155 and thus has the same contoured shape as the connection assembly 155, but is separated from the connection assembly 155 by a molded-in slot 156. The cantilevered region 157 has a proximal end 151 and a distal end 152, where the proximal end is nearer to the proximal end 141 of the male portion 140, but still remains within the connection assembly 155. The distal end 152 is near the distal end 142 of the male portion 140.

The molded-in slot 156 surrounds the cantilevered region 157 on three sides creating the cantilevered condition and causing the cantilevered region 157 to have a peninsula-like shape, which is wider at its distal end 152 than at its proximal end 151. The molded-in slot 156 surrounds the cantilevered region 157 along its proximal end 151 and along two sides generally oriented parallel to the longitudinal axis 143.

Figure 10:
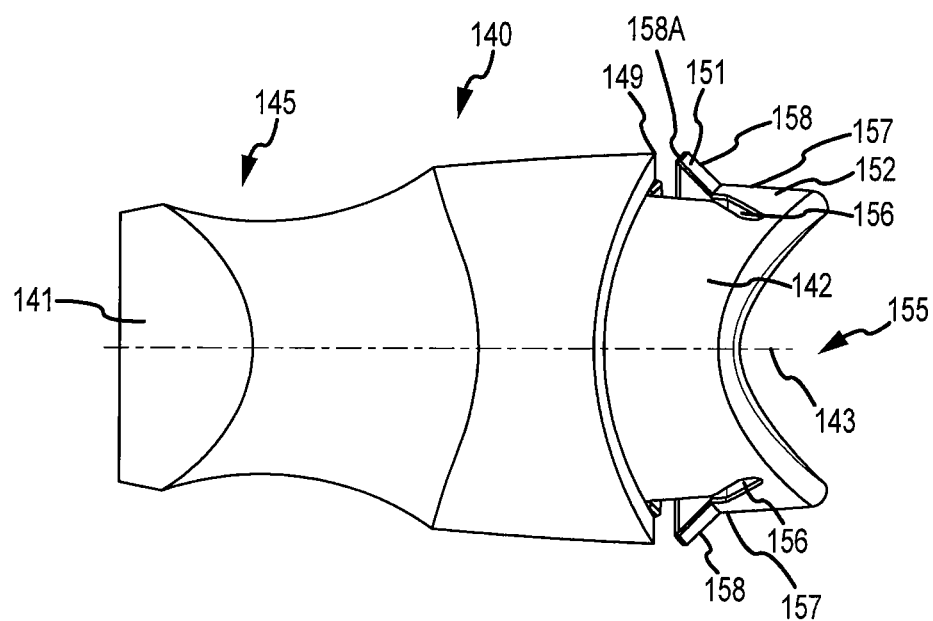
FIG. 10 is a left view of a male portion of a latch assembly according to certain embodiments.
Figure 11:
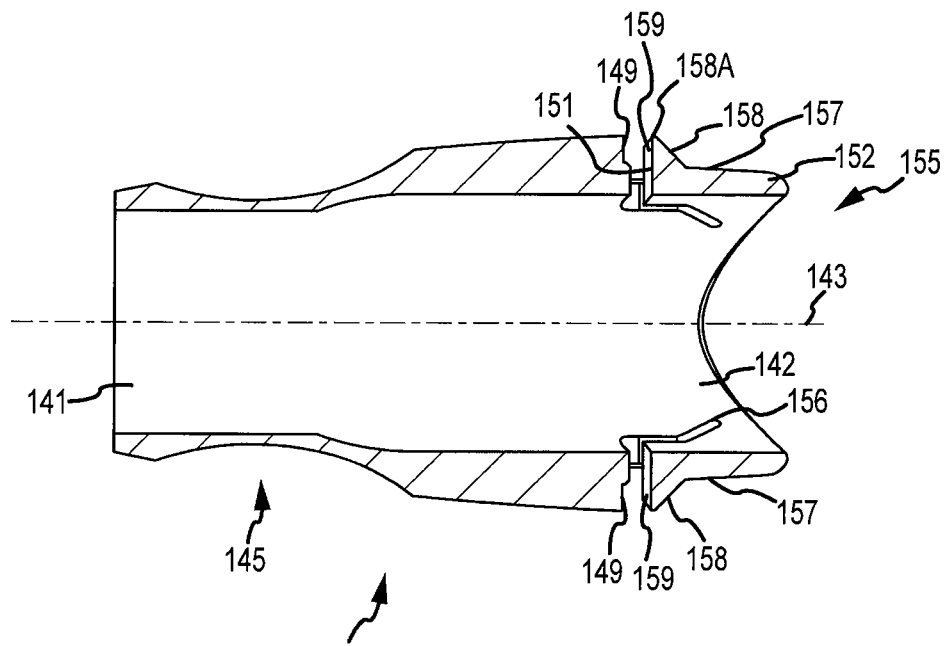
FIG. 11 is a left section view of a male portion of a latch assembly according to certain embodiments.
Figure 12:
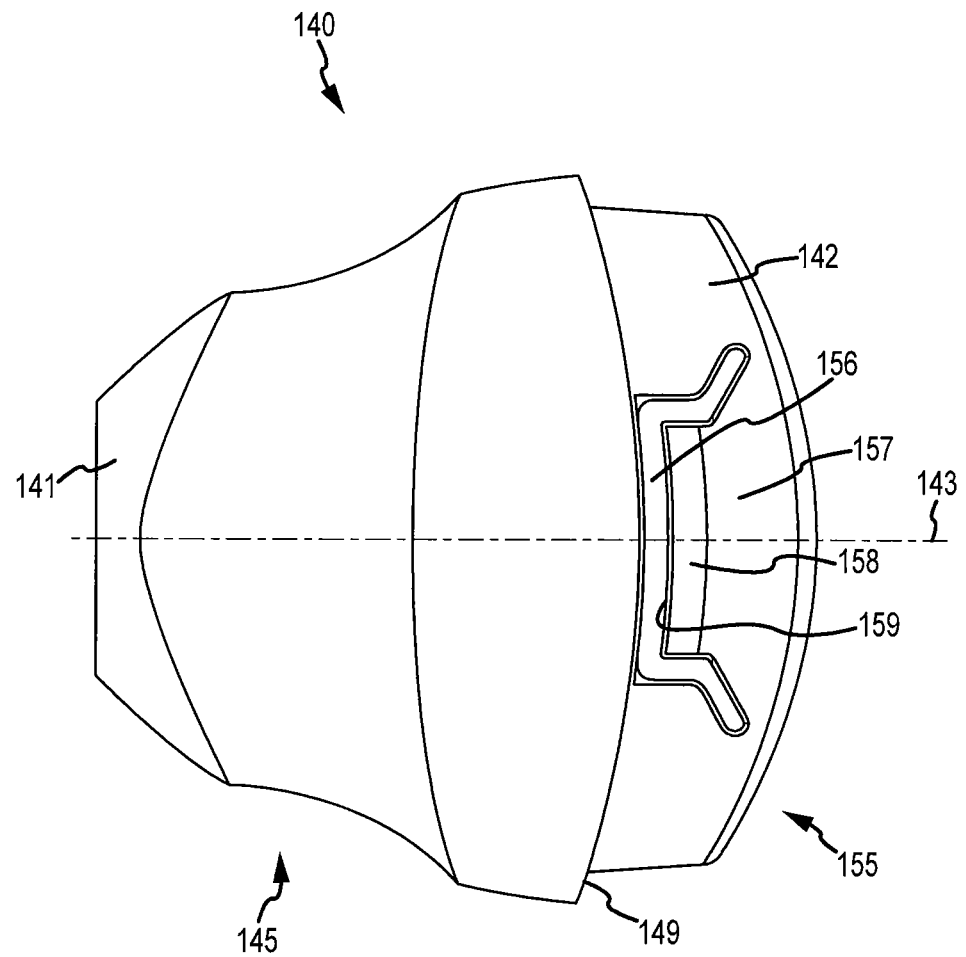
FIG. 12 is a top view of a male portion of a latch assembly according to certain embodiments.
Figure 13:
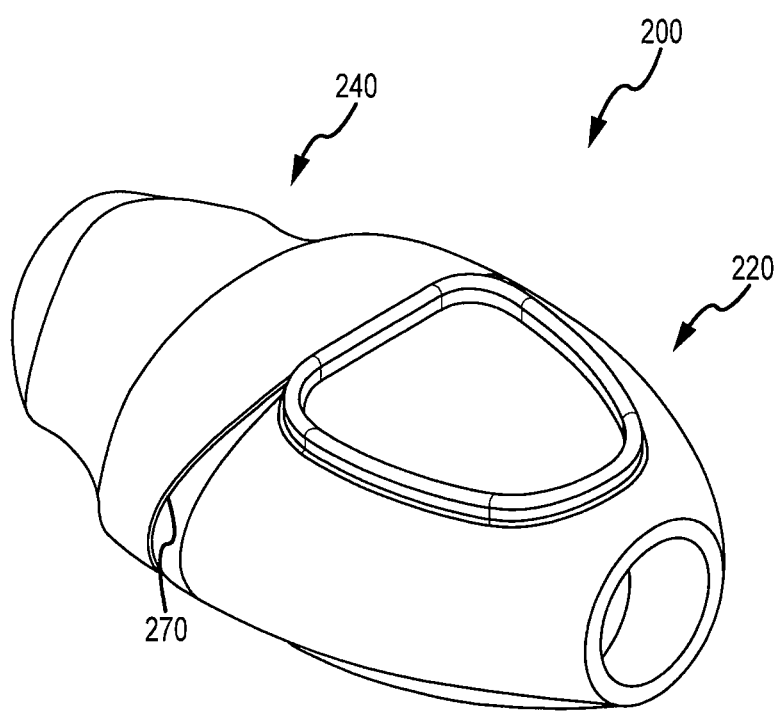
FIG. 13 is an isometric view of a latch assembly according to certain embodiments.
Figure 14:
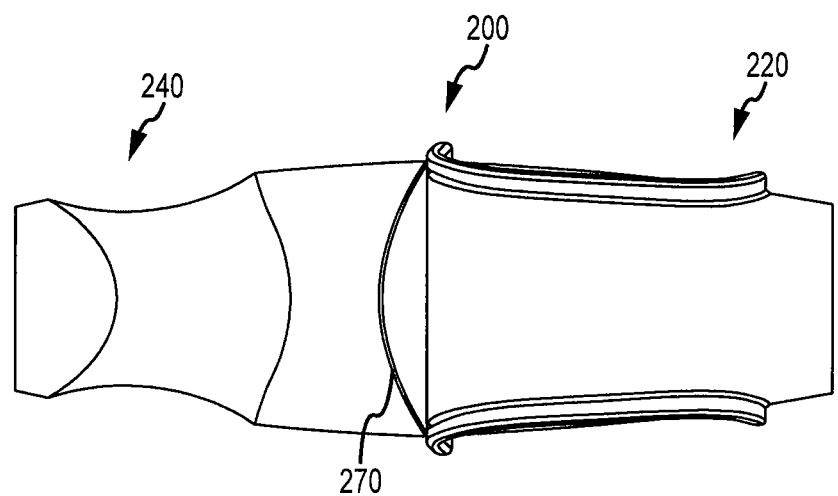
FIG. 14 is a left view of a latch assembly according to certain embodiments.

At the proximal end 151 of the cantilevered region 157, a ramped engagement feature 158 is shown. As best shown in FIGS. 10 and 11, the ramped engagement feature 158 slopes outwardly, relative to the inner volume of the male portion 140 as it extends toward the proximal end 151 of the cantilevered region 157. Thus, when an object, resistant to deflection, slides along the surface of the cantilevered portion 157 from its distal end 152 to its proximal end 151, the object will encounter the ramped engagement feature 158. As the object continues to slide along the cantilevered region 157, the object will interact with the sloping surface of the ramped engagement feature 158 causing the proximal end 151 of the cantilevered region 157 to flex into the inner volume of the male portion 140.

As best shown in FIG. 11, a latching face 159 of the ramped engagement feature 158 is provided and is defined as the vertical face beyond the end of the ramped portion of the ramped engagement feature 158. The latching face 159 is shown opposing the abutment face 149 and separated from the abutment face 149 by a portion of the connection assembly 155 and the molded-in slot 156. The ramped portion of the ramped engagement feature 158 and the latching face 159 come together at a point or ridge 158A.

In the present embodiment, the width of the ridge 158A, measured perpendicular to the longitudinal axis 143, is shorter than the portion of the molded-in slot 136 along the distal end 132 of the release button 137 of the female portion 120. This is so the ridge 158A of the ramped engagement feature 138 can penetrate the molded-in slot 136 when the male portion 140 and female portion 120 are connected, as will be explained in more detail below.

Having described the female portion 120 and the male portion 140 in great detail, reference is again made to FIGS. 1-4 showing the latch assembly 100. The female portion 120 and the male portion 140 may be connected together in mating relationship. When the two portions are connected, the abutment face 129 of the female portion abuts against the abutment face 149 of the male portion creating a seam 170 and preventing the two portions 120 and 140 from advancing any further toward one another.

Figure 3:
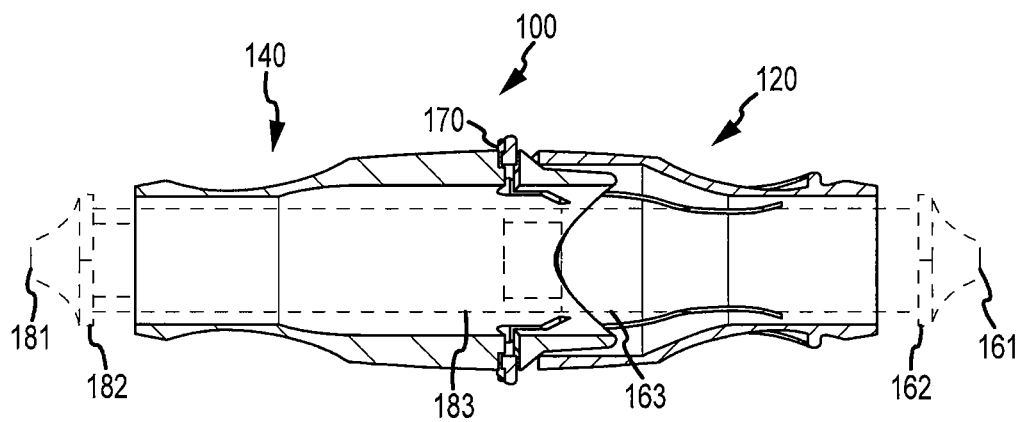
FIG. 3 is a left section view of a latch assembly according to certain embodiments.
Figure 4:
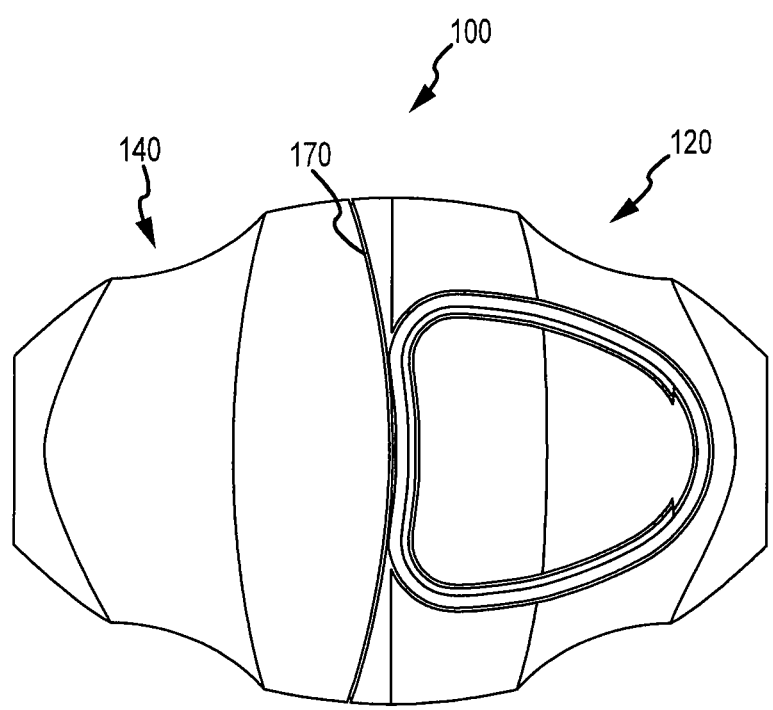
FIG. 4 is a top view of a latch assembly according to certain embodiments.
Figure 5:
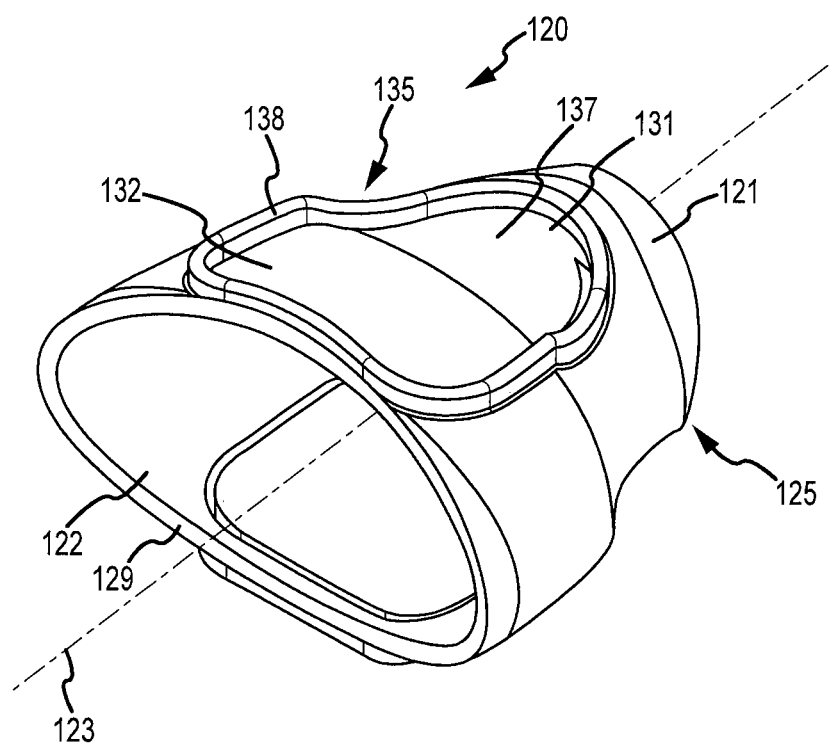
FIG. 5 is an isometric view of a female portion of a latch assembly according to certain embodiments.
Figure 6:
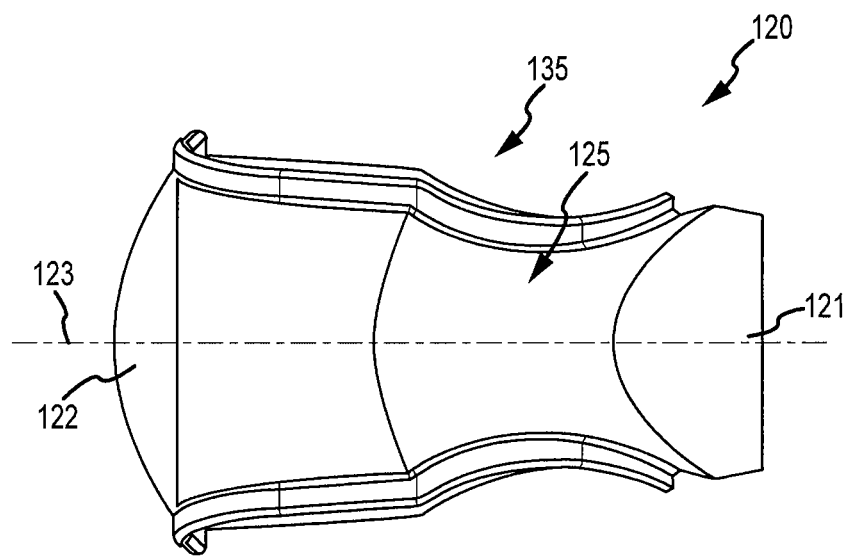
FIG. 6 is a left view of a female portion of a latch assembly according to certain embodiments.

Reference is now made particularly to FIG. 3 for describing in greater detail the latching nature of the connection between the female portion 120 and the male portion 140. As the distal ends 122 and 142 of the two portions 120 and 140 are brought together in opposing fashion, the connection assembly 155 of the male portion 140 is inserted into the female portion 120. As this occurs, the inner surface of the shell 125 passes along the surface of the connection assembly 155 and thus passes along the surface of the cantilevered region 157 and eventually encounters the ramped engagement feature 158. As the two portions 120 and 140 continue to be advanced toward each other, the interaction of the inner surface of the shell 125 with the ramped engagement feature 158, causes the proximal end 151 of the cantilevered region 157 to deflect into the inner volume of the male portion 140. It is noted that the portion of the shell 125 between the molded-in slot 136 and the distal end 122 is minimal providing only a narrow strip of material to press against the ramped engagement feature. However this strip is reinforced by the raised rib 138 and also can rely to a certain extend on the tensile hoop stresses developed in the shell as the two portions are assembled. As the two portions continue to advance toward each other, the cantilevered region 157 deflects sufficiently for the ridge 158A of the ramped engagement feature 158 to clear the inner surface of the shell 125, thus allowing for complete advancement of the female portion 120 and male portion 140 toward one another and bringing abutment face 129 into contact with abutment face 149 preventing further advancement. At the same time, the ramped engagement feature 158 passes within the volume defined by the shell 125 and encounters the molded-in slot 136. The ridge 158A of the ramped engagement feature 158 enters the molded-in slot 136 allowing the cantilevered region 157 to spring back into its non-deflected position. As this occurs, the latching face 159 of the ramped engagement feature 158 is brought into abutting relationship with the side face 139 of the raised rib 138 creating a latched condition in which the two portions 120 and 140 are releasably connected.

To release the female and male portions 120, 140 the release button 137 may be pressed. In so doing, as can be seen in FIG. 3, the release button 137 engages the ramped engagement feature 158 and the distal ends of both the release button 137 of the female portion 120 and the cantilevered region 157 of the male portion 140 deflect into the inner volume of their associated shells. When the release button is pressed with sufficient force, the cantilevered region 157 deflects sufficiently that the ramped engagement feature 158 clears the inner surface of the shell 125 allowing for separation of the two portions 120 and 140. It is noted here that the sloping surface of the ramped engagement feature 158 together with the downward force from the release button 137 creates a separation force such that when the ramped engagement feature 158 clears the bottom surface of the shell 125, the two portions 120 and 140 are biased toward separation and thus a separate tensile force may not be required to separate the two portions 120 and 140.

FIGS. 13-16 show a latch assembly 200 according to certain embodiments. In one embodiment, the latch assembly includes a female portion 220 and a male portion 240, which latch together to form a seam 270. Conduits 260 and 280 similar to those shown in FIGS. 1 and 3 are included, but are not shown for clarity.

FIGS. 17-20 show the female portion 220 of the embodiment shown in FIGS. 13-16 in greater detail. The female portion 220 of the latch assembly 200 is shown to have a proximal end 221 and a distal end 222. The female portion 220 is also shown to include a shell 225 and a connection opening 235 with an associated raised rib 238.

In the present embodiment, the shell 225 of the female portion 220 has a longitudinal axis 223. The shell 225 is generally hollow with a varying oblong shaped cross-section when viewed along the longitudinal axis 223. The cross-section varies from relatively narrow at its proximal end 221 to relatively broad at its distal end 222. The shell includes an opening/connection for a conduit at its proximal end. The shell further includes an abutment face 229 at the distal end 222, following the perimeter contour of the shell 225. Those skilled in the art will understand and appreciate that virtually any shaped cross-section can be used including, but not limited to, circular, square, and rectangular shapes.

Figure 17:
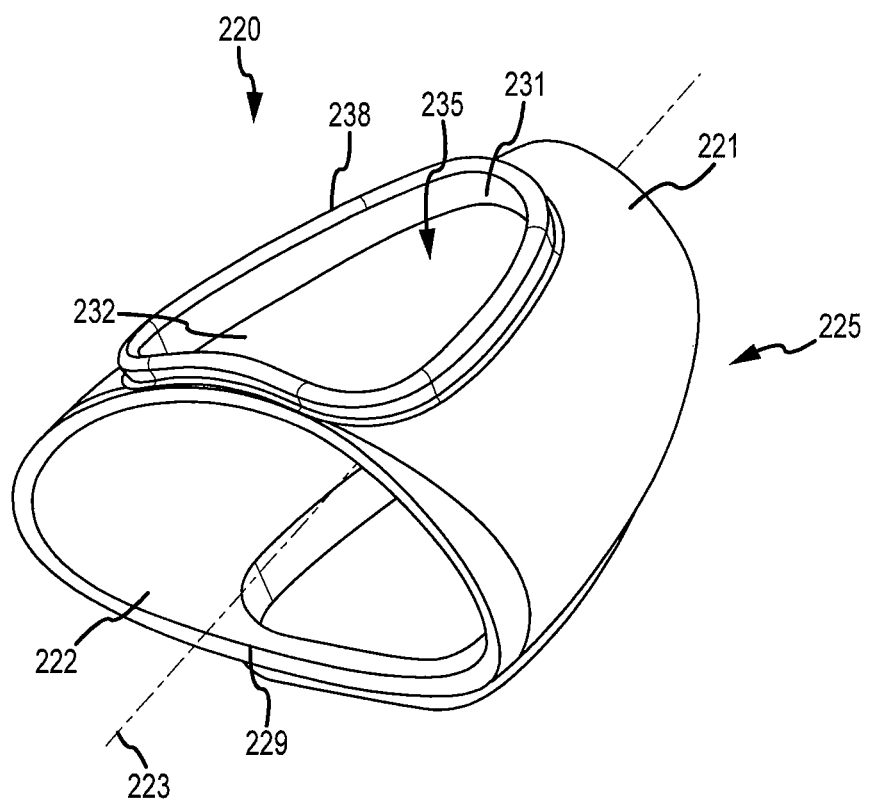
FIG. 17 is an isometric view of a female portion of a latch assembly according to certain embodiments.
Figure 18:
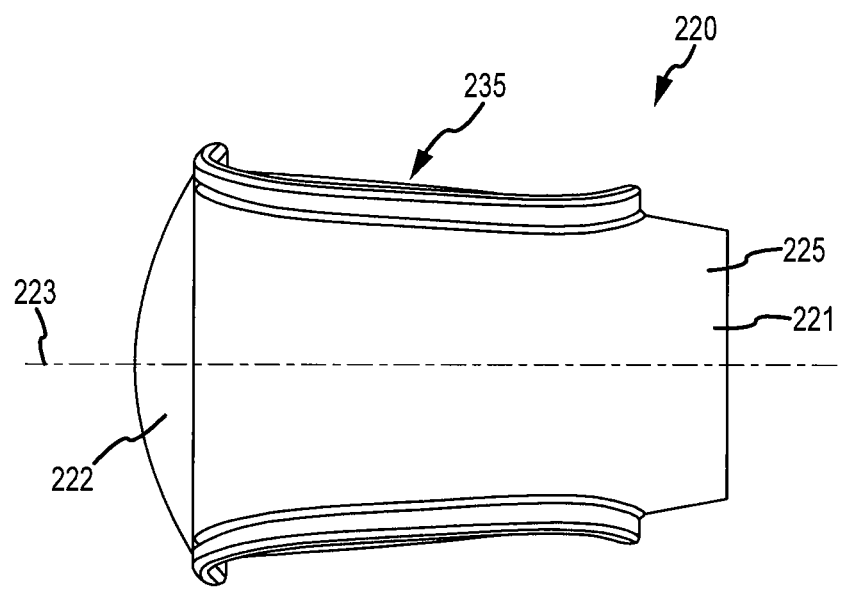
FIG. 18 is a left view of a female portion of a latch assembly according to certain embodiments.
Figure 19:
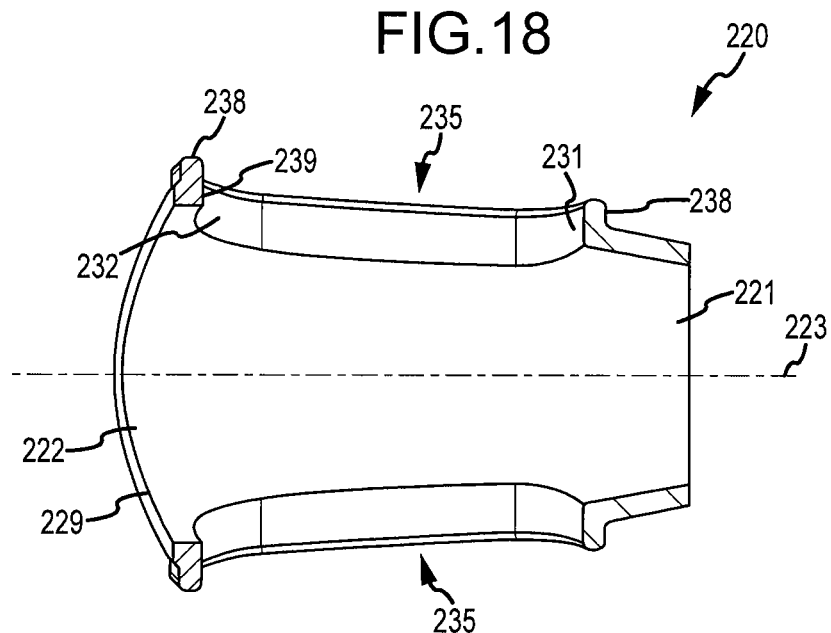
FIG. 19 is a left section view of a female portion of a latch assembly according to certain embodiments.
Figure 20:
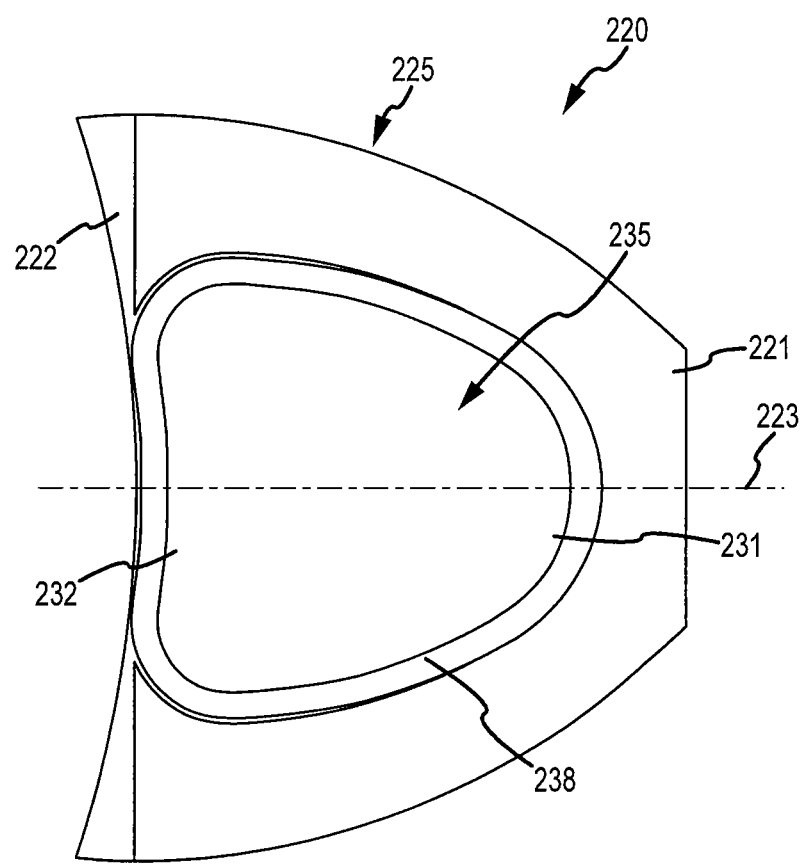
FIG. 20 is a top view of a female portion of a latch assembly according to certain embodiments.
Figure 21:
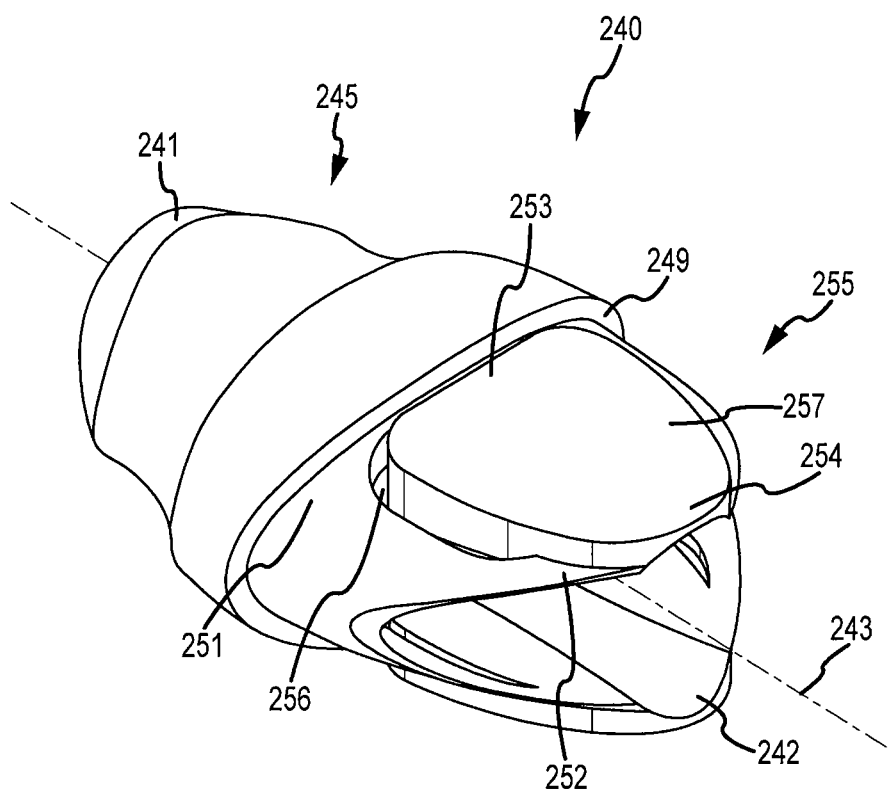
FIG. 21 is an isometric view of a male portion of a latch assembly according to certain embodiments.

In the present embodiment, the connection opening 235 of the female portion 220 is best shown in FIGS. 17 and 20 and is shaped to receive a release button 257 of the male portion 240, described below. It is noted that the present embodiment includes two connection openings 235 located on opposing surfaces of the female portion 220. For purpose of description, only one of the connection openings 235 is described herein. The connection opening 235 has a proximal end 231 and a distal end 232, where the proximal end 231 is near the proximal end 221 of the female portion 220 and the distal end 232 is near the distal end 222 of the female portion 220. The connection opening 235 is surrounded by a raised rib 238 with a side face 239 defining the outer perimeter of the connection opening 235. The connection opening is narrower at its proximal end 231 than at its distal end 232 and is shaped with smooth corners.

FIGS. 21-24 show the male portion 240 of the embodiment shown in FIGS. 13-16 in greater detail. The male portion 240 of the latch assembly 200 is shown to have a proximal end 241 and a distal end 242. The male portion 240 is also shown to include a shell 245 and a connection assembly 255.

In the present embodiment, the shell 245 has a longitudinal axis 243. The shell 245 is generally hollow with a varying oblong shaped cross-section when viewed along the longitudinal axis 243. The outer contour of the shell 245 at its distal end matches the outer contour of the shell 225 at its distal end 222. As with the latch assembly 100, this provides for a smooth surface transition between the female 220 and male 240 portions of the latch assembly 200. The cross-section of the shell 245 varies from relatively narrow at its proximal end 241 to relatively broad at its distal end. The shell 245 includes an exit opening/connection for a conduit at the proximal end 241. Those skilled in the art will understand and appreciate that virtually any shaped cross-section can be used including, but not limited to circular, square, and rectangular shapes. Those skilled in the art will also understand and appreciate that a smooth transition may not always be necessary or desired and thus the outer contour of the shell 225 and the shell 245 would not need to match.

In the present embodiment, the connection assembly 255 of the male portion 240 is situated at the distal end of the male portion 240 and is separated from the shell 245 by an abutment face 249. The connection assembly 255 comprises a necked-down section of the shell 245 such that the outer contour of the connection assembly 255 substantially matches the inner contour of the shell 225 of the female portion 220. This provides for a mating relationship between the female portion 220 and the male portion 240 where the connection assembly 255 extends within the shell 225.

In contrast to the embodiment shown in FIGS. 1-12, the connection assembly 255 extends into the female portion 220 further than the connection assembly 155 extends into the female portion 120. In the present embodiment, the connection assembly 255 extends substantially as far as the proximal end 231 of the connection opening 235 of the female portion 220 when connected. The connection assembly 255 has a proximal end 251 and a distal end 252, where the proximal end 251 is adjacent the abutment face 249 and the distal end 252 extends to the distal end 242 of the male portion 240.

The connection assembly 255 further comprises a release button 257 supported near the distal end 252. It is noted that the connection assembly 255 includes two release buttons 257 located on opposing surfaces of the connection assembly 255. For purposes of description, only one of the release buttons 257 is described herein. The release button 257 has a shape substantially matching that of the connection opening 235 and a surface contour substantially matching that of the shell 225 of the female portion 220. Thus, the release button 257 is raised above the necked-down surface of the connection assembly 255 so as to match the contour of the shell 225. The release button 257 extends proximally from the distal end 252 of the connection assembly 255 and is separated from the connection assembly 255 by a molded-in slot 256. The release button 257 has a proximal end 253 and a distal end 254, where the proximal end 253 is near the proximal end 251 of the connection assembly 255 and the distal end 254 is near the distal end 252 of the connection assembly 255.

In the present embodiment, the molded-in slot 256 surrounds the release button 257 on three sides creating the cantilevered condition and causing the release button 257 to have a peninsula-like shape matching that of the connection opening 235. The molded-in slot 256 surrounds the release button 257 on the proximal end 253 and two sides generally oriented parallel to the longitudinal axis 243.

Figure 22:
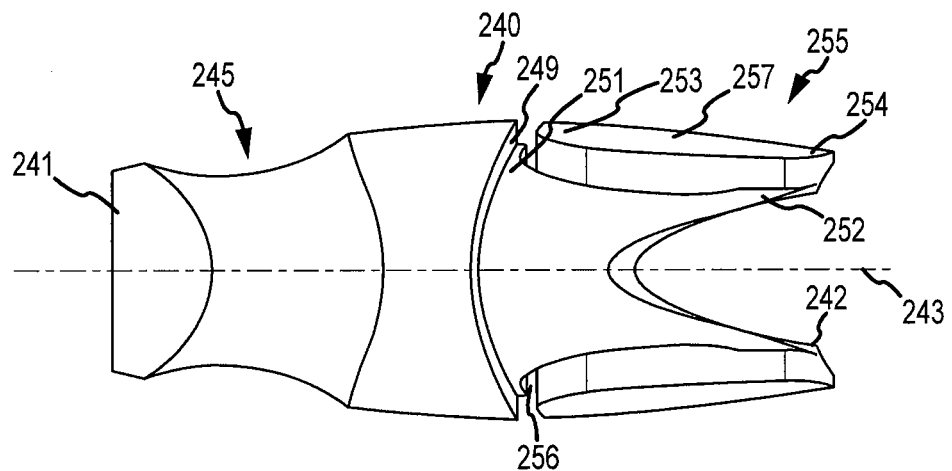
FIG. 22 is a left view of a male portion of a latch assembly according to certain embodiments.
Figure 23:
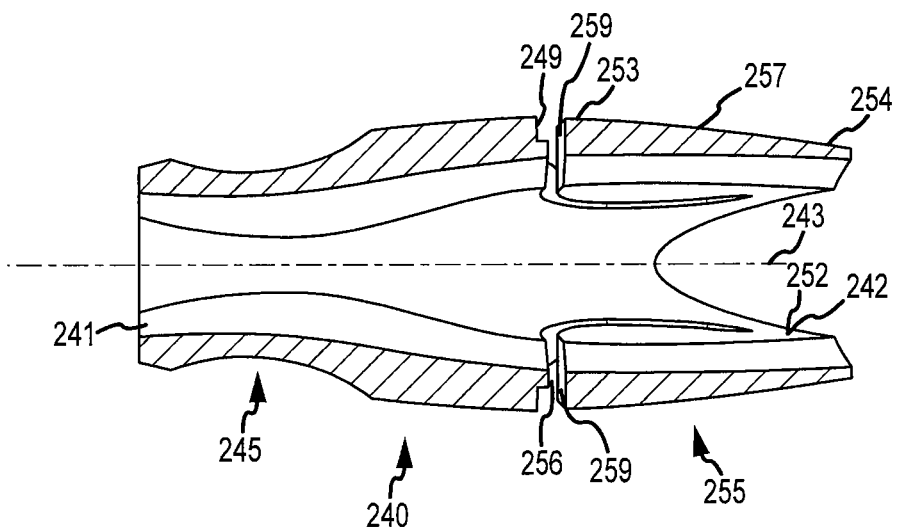
FIG. 23 is a left section view of a male portion of a latch assembly according to certain embodiments.
Figure 24:
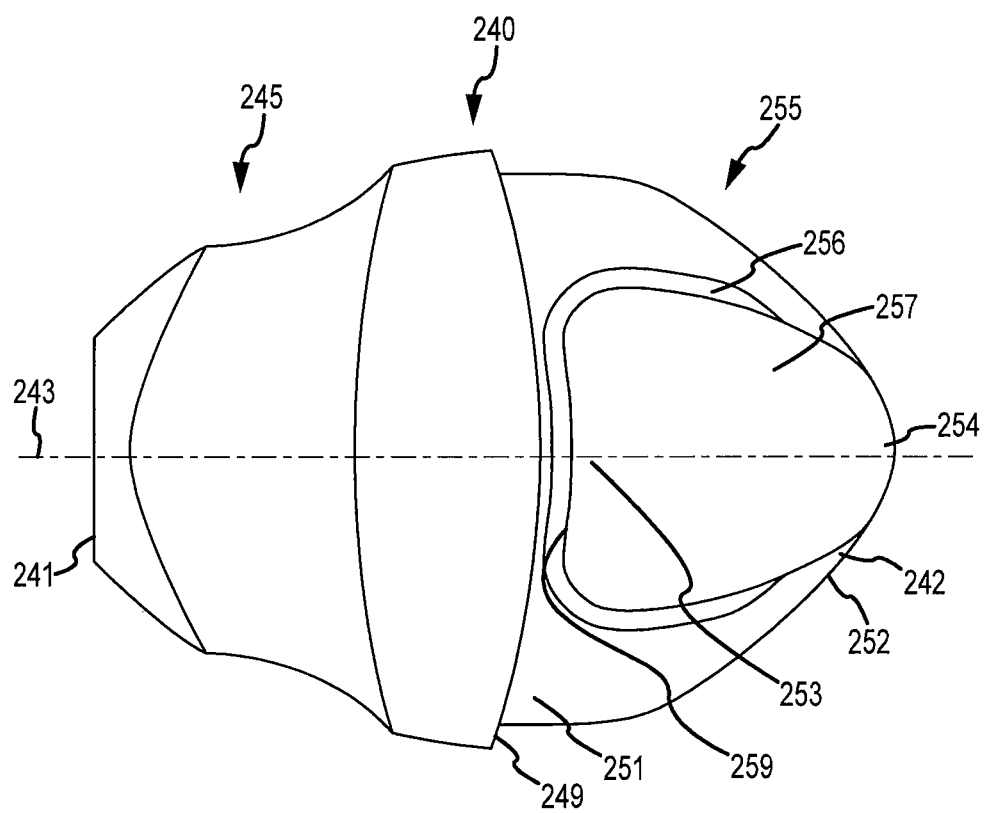
FIG. 24 is a top view of a male portion of a latch assembly according to certain embodiments.
Figure 25:
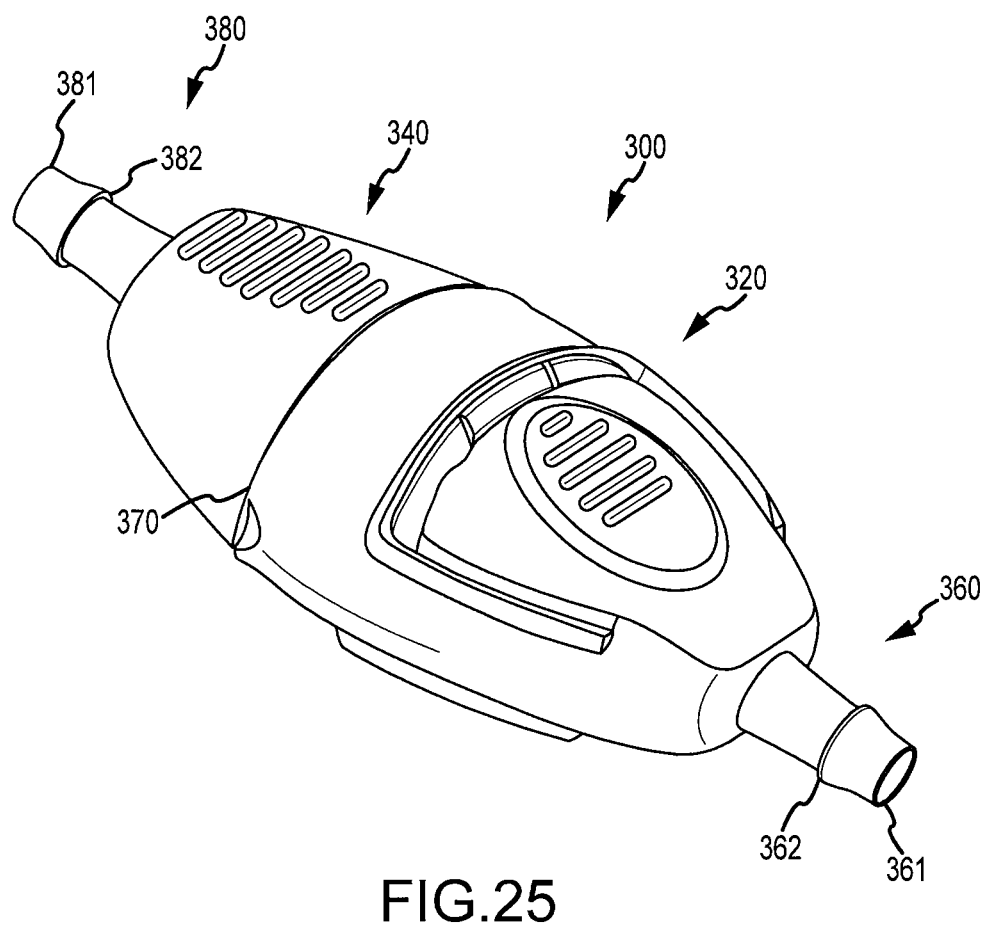
FIG. 25 is an isometric view of a latch assembly according to certain embodiments.
Figure 26:
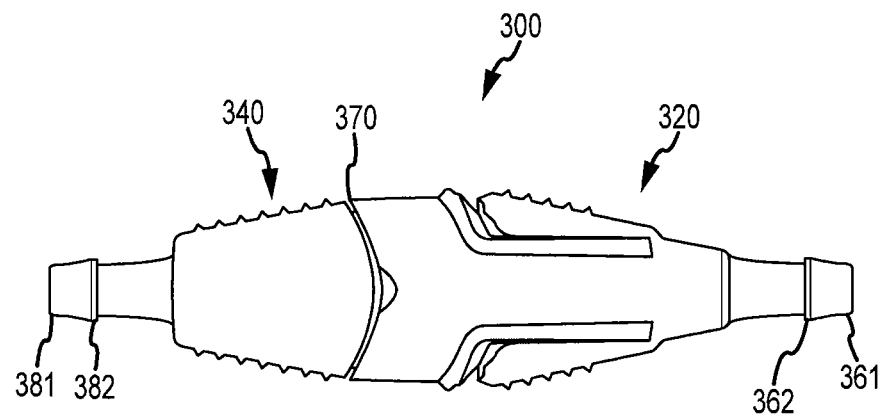
FIG. 26 is a left view of a latch assembly according to certain embodiments.
Figure 27:
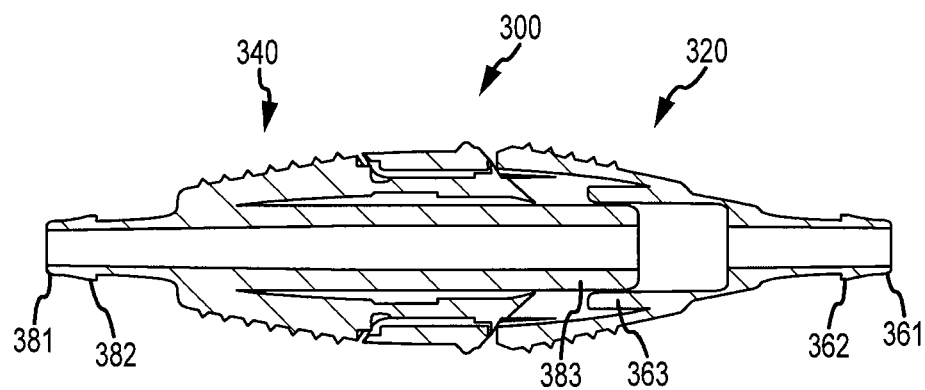
FIG. 27 is a left section view of a latch assembly according to certain embodiments.
Figure 28:
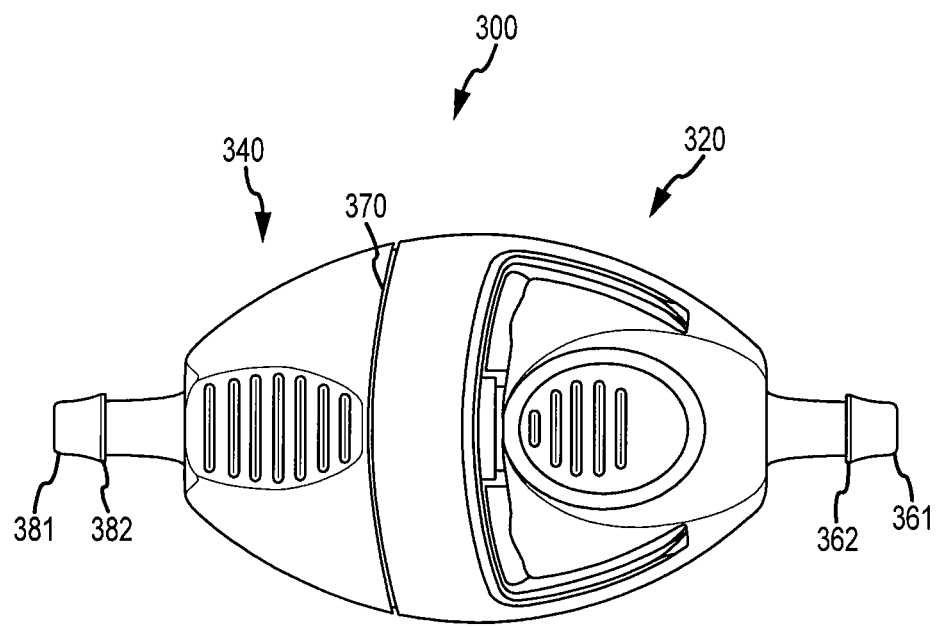
FIG. 28 is a top view of a latch assembly according to certain embodiments.

As best shown in FIGS. 22 and 23, the release button 257 slopes gradually outward, relative to the internal space defined by the shell 245, as the button extends from its distal end 254 toward its proximal end 253. Thus, when an object resistant to deflection slides along the surface of the release button 257 from its distal end 254 to its proximal end 253, the object will cause the release button 257 to flex into the inner volume of the male portion 240 due to its cantilevered condition and slope.

As best shown in FIG. 23, a latching face 259 is provided and is defined as the generally vertical face along the proximal end 253 of the release button 257. The latching face 259 is shown opposing the abutment face 249 and separated from the abutment face 249 by a portion of the connection assembly 255 and the molded-in slot 256.

Having described the female portion 220 and the male portion 240 in great detail, reference is again made to FIGS. 13-16 showing the latch assembly 200. The female portion 220 and the male portion 240 may be connected together in mating relationship. When the two portions are connected, the abutment face 229 of the female portion 220 abuts against the abutment face 249 of the male portion 240 creating a seam 270 and preventing the two portions 220 and 240 from advancing any further towards one another.

Figure 15:
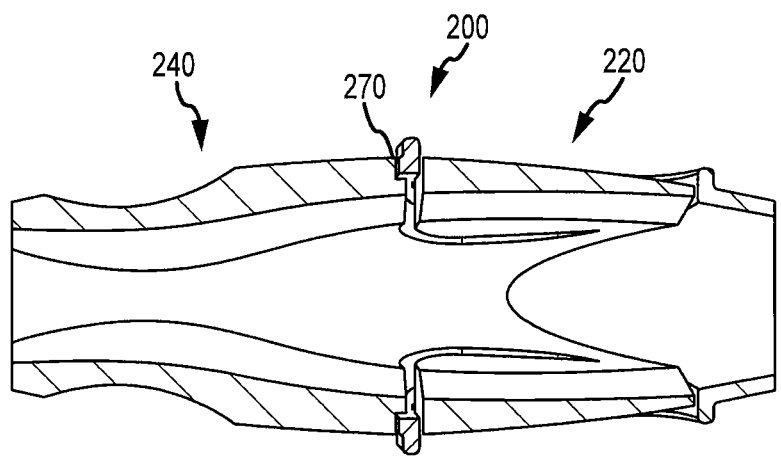
FIG. 15 is a left section view of a latch assembly according to certain embodiments.
Figure 16:
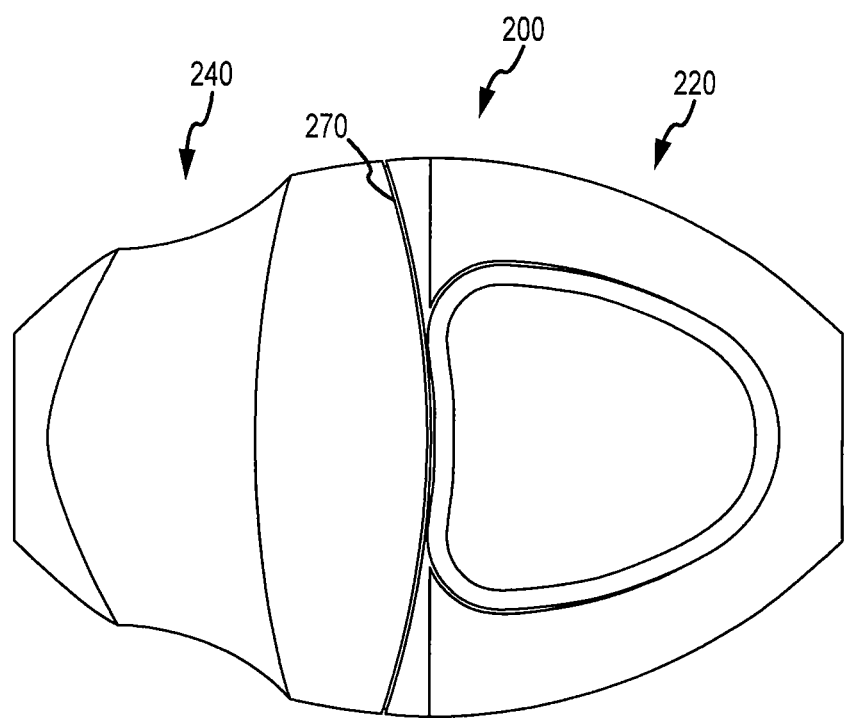
FIG. 16 is a top view of a latch assembly according to certain embodiments.

Reference is now made to FIG. 15 for describing in greater detail the latching nature of the connection between the female portion 220 and the male portion 240. As the distal ends 222 and 242 of the two portions 220 and 240 are brought together in opposing fashion, the connection assembly 255 of the male portion 240 is inserted into the female portion 220. As this occurs, the inner surface of the shell 225 passes along the surface of the release button 257 causing it to deflect into the inner portion of the male portion 240 and allowing the two portions 220 and 240 to continue to advance towards each other until the abutment faces 229 and 249 are in contact. As with latch assembly 100, the portion of the shell 225 between the connection opening 235 and the distal end 222 is minimal providing only a narrow strip of material to press against the release button 257. However this strip is reinforced by the raised rib 238 and also can rely to a certain extend on the tensile hoop stresses developed in the shell as the two portions are assembled. As the abutment faces 229 and 249 are brought into contact, the release button 257 comes into alignment with the connection opening 235 allowing the release button 257 to spring back into its non-deflected shape. In so doing, the latching face 259 of release button 257 is brought into abutting relationship with the side face 239 of the raise rib 238 creating a latched condition in which the two portions 220 and 240 are releasably connected.

To release the female and male portions 220, 240 the release button 257 may be pressed. In so doing, as can be seen in FIG. 15, the release button 257 deflects sufficiently that the latching face 259 is no longer in abutting relationship with the side face 239 of the raise rib 238 thus allowing for separation of the two portions 220 and 240.

FIGS. 25-28 show yet another latch assembly 300 according to certain embodiments. The latch assembly 300 resembles latch assembly 100 in certain respects and also includes some distinct differences as discussed below.

The latch assembly 300 includes a female portion 320 and a male portion 340, which latch together to form a seam 370. Conduits 360 and 380 similar to those shown in FIGS. 1 and 3 are also included. Each conduit 360 and 380 includes a respective set of proximal ends 361 and 381 respectively having hose barbs 362 and 382. Each conduit 360 and 380 also includes a respective distal end 363 and 383, which are configured to mate in a male/female mating arrangement.

While in one embodiment, hose barbs 362, 382 may be provided for joining the proximal ends 361, 381 to polymer tubing, in other embodiments, the proximal ends 361, 381 may be provided with other joining features, such as threads, flanges, couplings, clamps, etc.

FIGS. 29-32 show the female portion 320 of the present embodiment. The female portion 320 has a proximal end 321, distal end 322, a shell 325, and a connection assembly 335. The shell 325 has a longitudinal axis 323 and a hollow, varying, oblong shaped cross-section. The shell 325 further includes an abutment face 329 at the distal end 322. The connection assemblies 335 of the female portion 320 comprise a release button 337, a molded-in slot 336, and a raised rib 338. The release button 337 comprises a section of the shell 325 following the contour of the shell 325 and is separated from the shell 325 by a molded-in slot 336 and a raise rib 338. The release button further has a proximal end 331 and a distal end 332. The release button 337 is surrounded by the molded-in slot 336 on three sides, two generally parallel to the longitudinal axis 323 and a third side along the release button's distal end 332. The molded-in slot 336 causes the release button 337 to have a peninsula-like shape and creates a cantilevered condition where the release button 337 is narrower at its proximal end 331 than at its distal end 332. This cantilevered condition allows the distal end 332 of the release button 337 to flex into the interior space of the female portion 320 when pressed on from the outer side. The raised rib 338, like raised rib 138 projects outwardly relative to the inner space of the female portion 320 and has a side face 339 defining the outer perimeter of the molded-in slot 336.

In contrast to latch assembly 100, the release button also includes a raised surface 337A and a raised pattern 337B. Also, the raised rib 338 is shown not to completely surround the release button 337 and only occurs on three sides of the release button. Moreover, the molded-in slot 336 does not extend as far around the release button so as to surround it on a fourth side, but is limited to three sides.

Additional elements shown in FIGS. 29-32 include alignment recesses 326, a molded-in slot divider 336A and molded-in slot receiving areas 336B. The alignment recesses 326 occur on the inner surface of the shell 325 and work to ensure alignment of the ramped engagement features 358 prior to full engagement of the male 340 and female 320 portions. The molded-in slot divider 336A is a projection proximally extending from the shell 325 partially across the molded-in slot 336. This projection breaks up the molded-in slot 336 creating molded-in slot receiving areas 336B for the ramped engagement features 358 to engage.

FIGS. 33-36 show the male portion 340 of the present embodiment. The male portion 340 has a proximal end 341, a distal end 342, a shell 345, and a connection assembly 355. The shell 345 has a longitudinal axis 343 and has a hollow, varying, oblong shaped cross-section. The outer contour of the shell 345 at its distal end matches the outer contour of the shell 325 at its distal end 322. The connection assembly 355 is situated at the distal end 342 and is separated from the shell 345 by an abutment face 349. The connection assembly 355 comprises a necked-down section of the shell 345. The outer contour of the connection assembly 355 substantially matches the inner contour of the shell 325 of the female portion 320 at its distal end 322 providing for a mating relationship. The connection assembly 355 further comprises a cantilevered region 357 and a ramped engagement feature 358. In the present embodiment, the connection assembly 355 includes four cantilevered regions 357. However, in other embodiments, there may a greater or lesser number of cantilevered regions 357. For purposes of description, only one of the cantilevered regions 357 is described herein.

The cantilevered region 357 is distinct from the cantilevered region 157 of latch assembly 100 in several respects. First, the cantilevered region is further necked down from the connection assembly. Second, the cantilevered region 357 is fixed to the connection assembly 355 at the cantilevered region's proximal end 351 rather than its distal end 352. Third, the ramped engagement feature 358 is located at the cantilevered region's distal end 352 rather than its proximal end 351. However, the orientation of the ramped engagement feature 358 has remained the same in that the surface of the ramped engagement feature 358 slopes outwardly relative to the inner volume of the male portion 340 as the surface extends from its distal end to its proximal end. An additional distinction of the latch assembly 300 from latch assembly 100 is that the surface of the ramped engagement feature 358 is convex.

Figure 29:
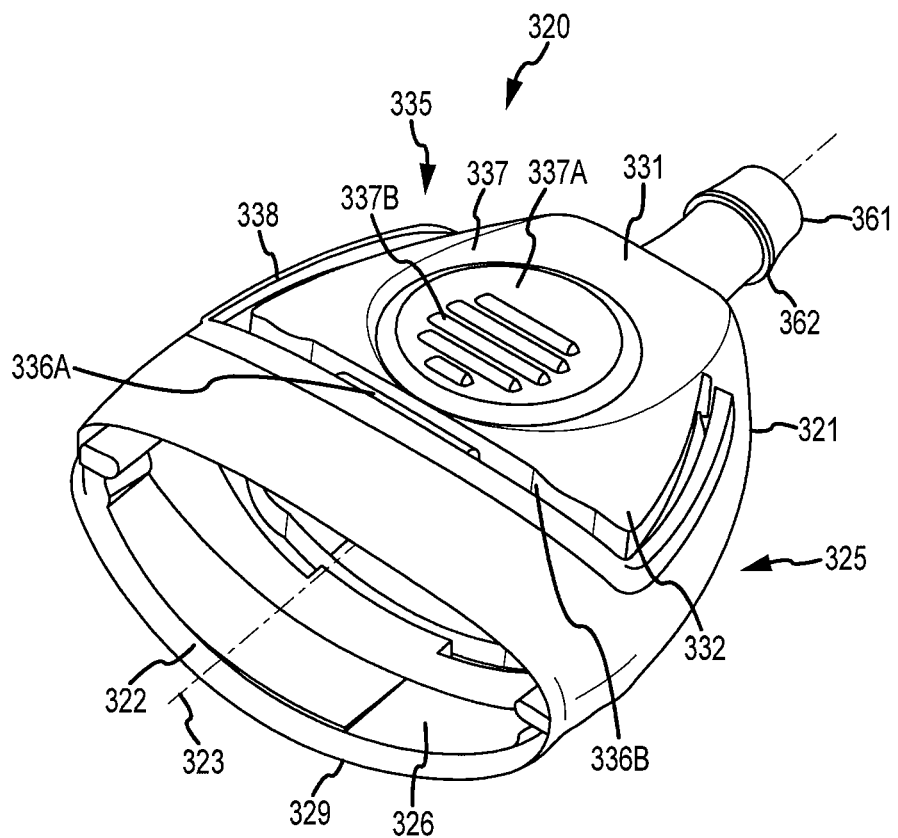
FIG. 29 is an isometric view of a female portion of a latch assembly according to certain embodiments.
Figure 30:
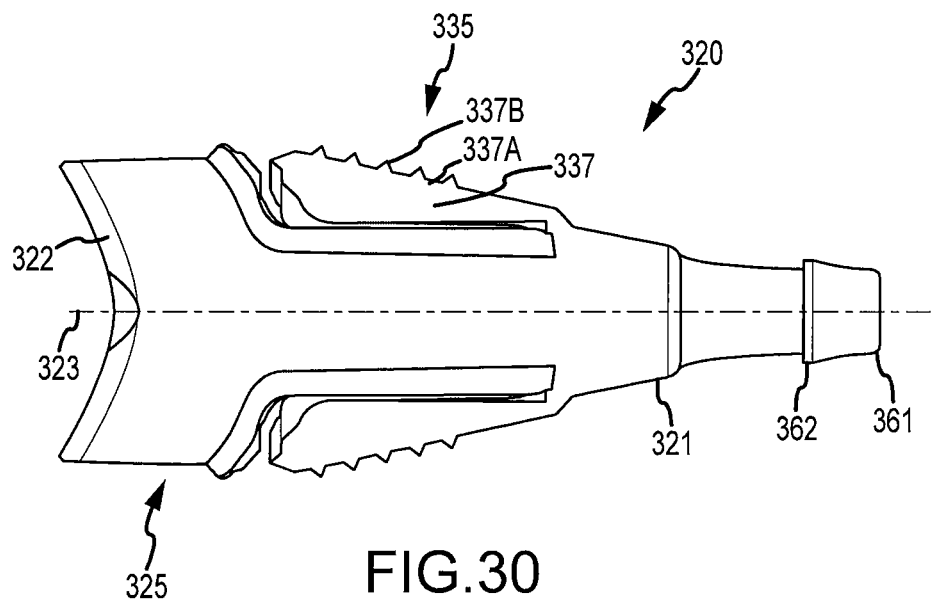
FIG. 30 is a left view of a female portion of a latch assembly according to certain embodiments.
Figure 31:
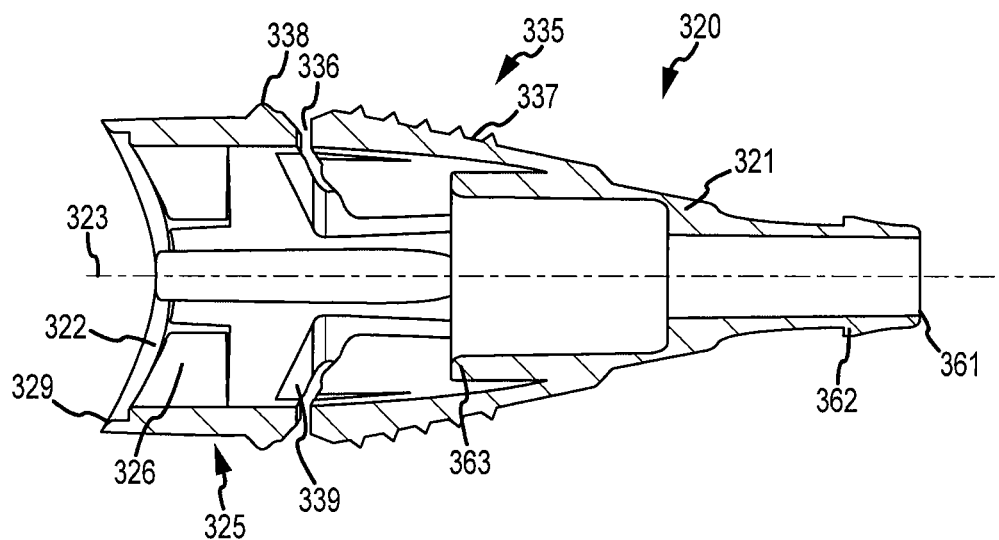
FIG. 31 is a left section view of a female portion of a latch assembly according to certain embodiments.
Figure 32:
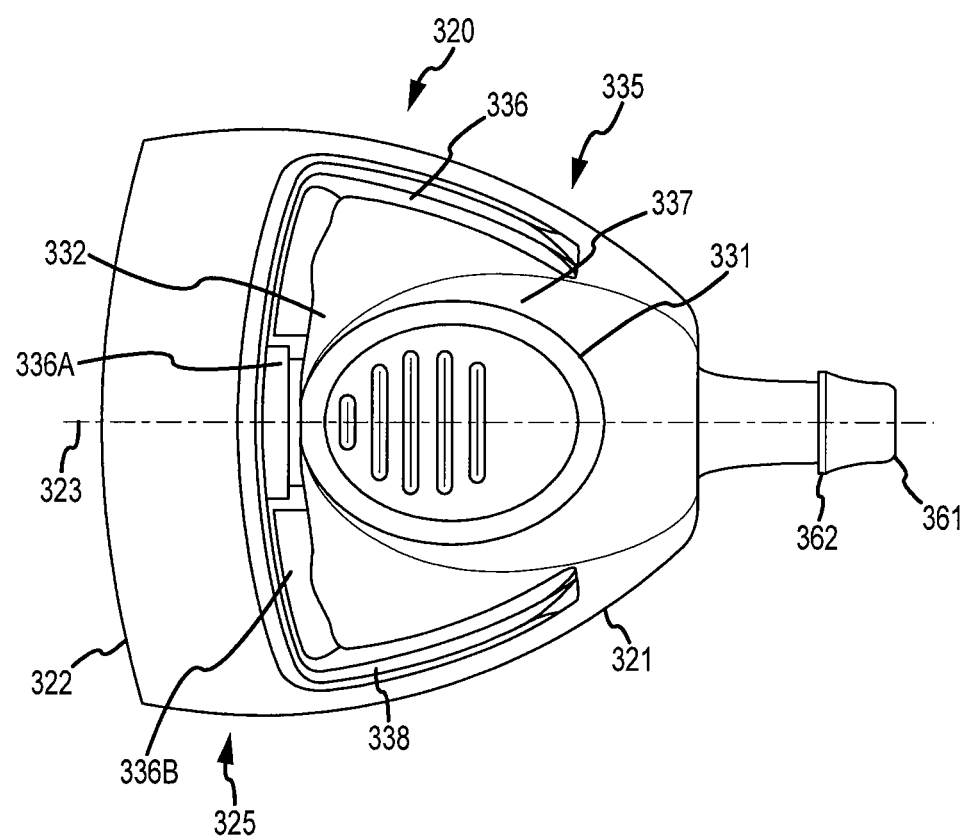
FIG. 32 is a top view of a female portion of a latch assembly according to certain embodiments.
Figure 33:
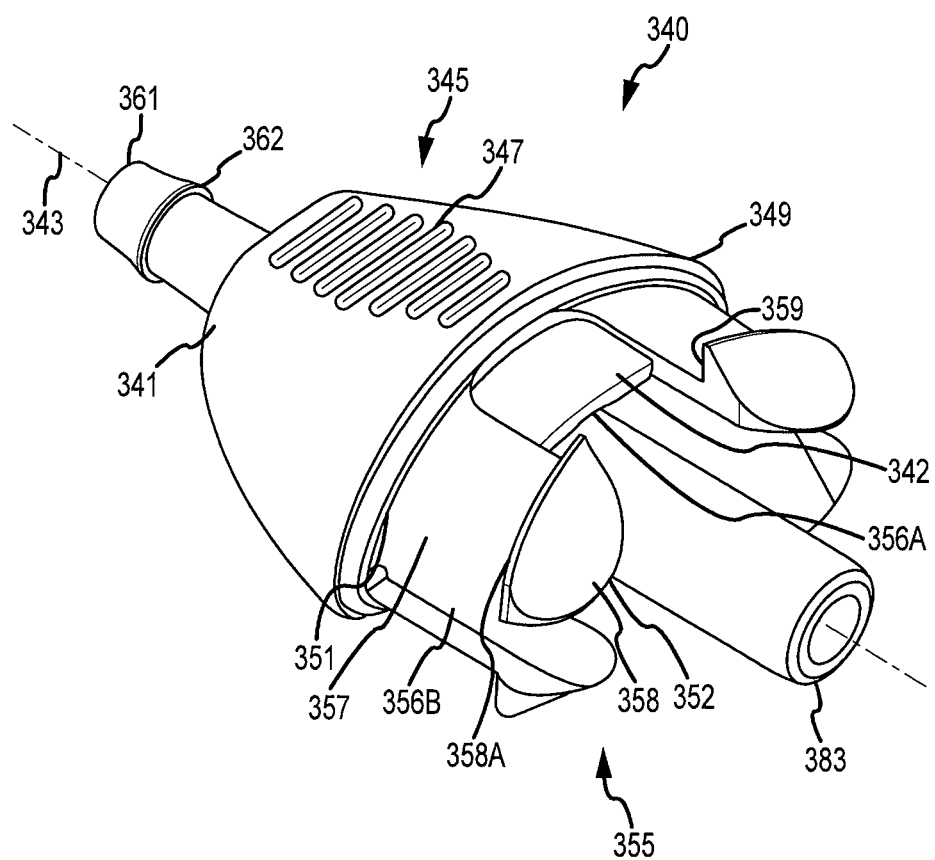
FIG. 33 is an isometric view of a male portion of a latch assembly according to certain embodiments.
Figure 34:
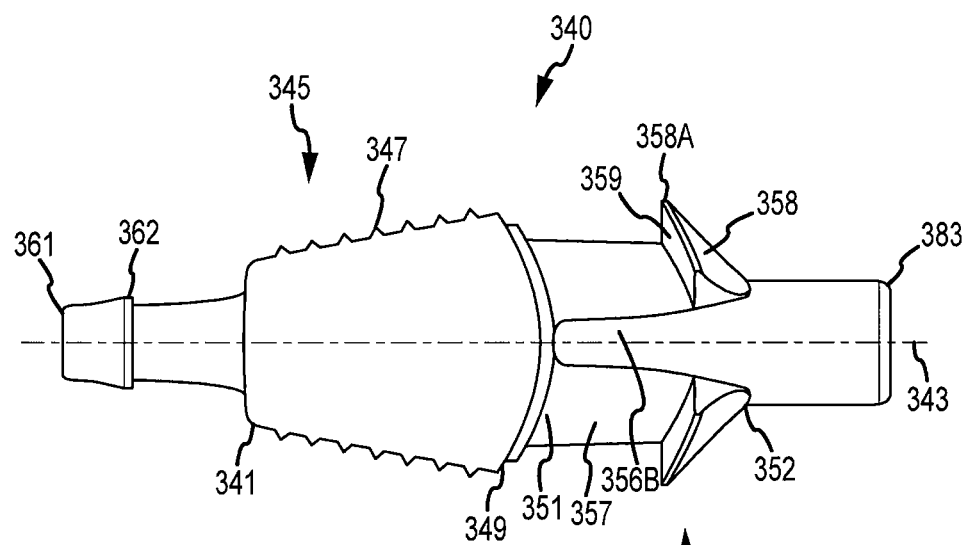
FIG. 34 is a left view of a male portion of a latch assembly according to certain embodiments.
Figure 35:
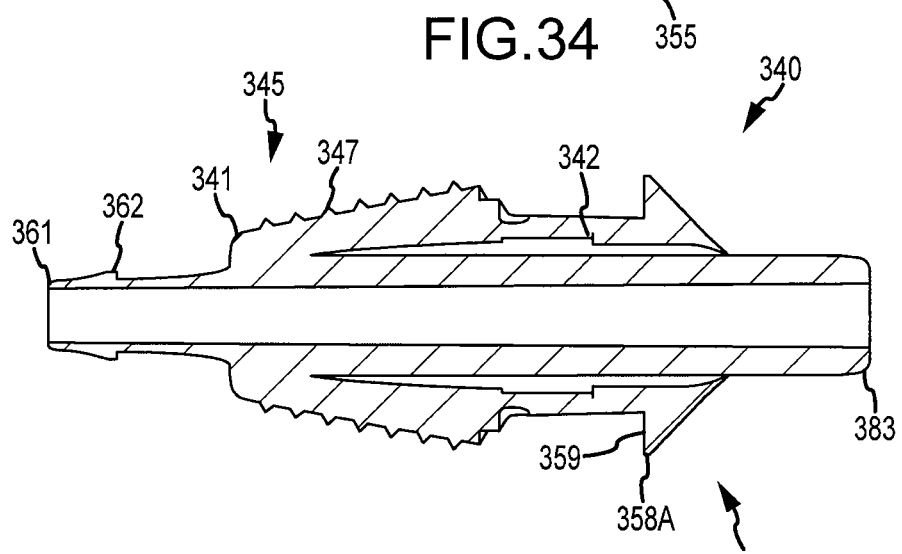
FIG. 35 is a left section view of a male portion of a latch assembly according to certain embodiments.
Figure 36:
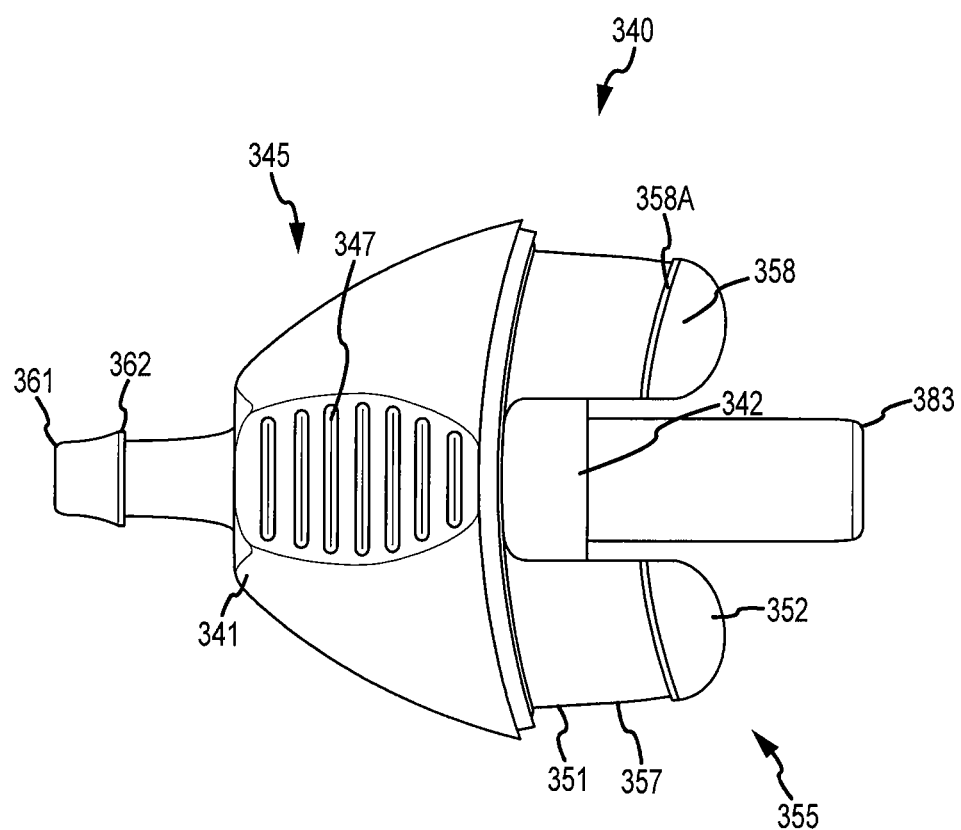
FIG. 36 is a top view of a male portion of a latch assembly according to certain embodiments.

The male portion 340 also includes raised surface features 347 on the shell 345. In addition, the connection assembly 355 includes cutaway recesses 356A on the inner surface which aid in minimizing the depth of the assembly while still accommodating the conduit. The connection assembly 355 also includes slits 356B along the sides of the connection assembly 355 separating two of the four cantilevered regions 357. These slits allow for easier deflection of the cantilevered region 357. Further to this idea of easier deflection of the cantilevered region 357, FIG. 29 shows a more substantial strip of material remaining between the molded-in slot 336 and the distal end 322 of the female portion 320. This causes this strip to be stiffer than that shown, for example, in FIG. 8 and adds to the ability of the device to cause deflection of the cantilevered region 357.

Also shown is a latching face 359 of the ramped engagement feature 358 defined as the generally vertical face beyond the end of the ramped portion of the ramped engagement feature 358. The latching face 359 is shown opposing the abutment face 349 and separated from the abutment face 349 by a length of the cantilevered region 357 and a portion of the connection assembly 355. The ramped portion of the ramped engagement feature 358 and the latching face 359 come together at a point or ridge 358A. The ridge 358A is adapted to fit into the molded-in slot receiving areas 3366.

As with latch assemblies 100 and 200, the female portion 320 and the male portion 340 may be connected together in mating relationship. As shown in FIGS. 25-28, when the two portions are connected, the abutment face 329 of the female portion abuts against the abutment face 349 of the male portion creating a seam 370 and preventing the two portions from advancing any further toward one another.

As the distal ends 322 and 342 of the two portions 320 and 340 are brought together in opposing fashion, the ramped engagement features 358 initially engage the alignment recesses 326. This initial contact aids the user in assuring that the two portions 320 and 340 are properly aligned. As the two portions continue to advance, the sloping surface of the ramped engagement feature 358 causes the cantilevered regions 357 to deflect until the entire ramped engagement feature 358 passes within the inner surface of the shell 325. This allows for complete advancement of the female portion 320 and male portion 340 toward one another and bringing abutment face 329 into contact with abutment face 349, preventing further advancement. At the same time, the ramped engagement feature 358 passes within the volume defined by the shell 325 and it encounters the molded-in slot receiving areas 336B. The ridge 358A of the ramped engagement feature 358 enters the molded-in slot receiving areas 336B allowing the cantilevered regions 357 to spring back into their non-deflected position. As this occurs, the latching face 359 of the ramped engagement feature 358 is brought into abutting relationship with the side face 339 of the raised rib 338 creating a latched condition in which the two portions 320 and 340 are releasably connected.

To release the female and male portions 320, 340 the release button 337 may be pressed. In so doing, the release button 337 engages the ramped engagement feature 358 and both the release button 337 and the cantilevered region 357 deflect into the inner volume of their associated shells. When the release button 337 is pressed with sufficient force, the cantilevered region 357 deflects sufficiently that the ramped engagement feature 358 clears the inner surface of the shell 325 allowing for separation of the two portions 320 and 340. As with latch assembly 100, the sloping surface of the ramped engagement feature 358 together with the downward force from the release button 337 creates a separation force such that when the ramped engagement feature 358 clears the bottom surface of the shell 325, the two portions 320 and 340 are biased toward separation and thus a separate tensile force may not be required to separate the two portions 320 and 340.

FIGS. 37-40 show yet another embodiment of a female portion 420 of a latch assembly. The female portion 420 of the latch assembly shown in FIGS. 37-40 resembles the female portion 320 of latch assembly 300 in most respects and a corresponding male portion 440 is not shown. As such, the female portion 420 will be described as interacting with male portion 340.

Figure 37:
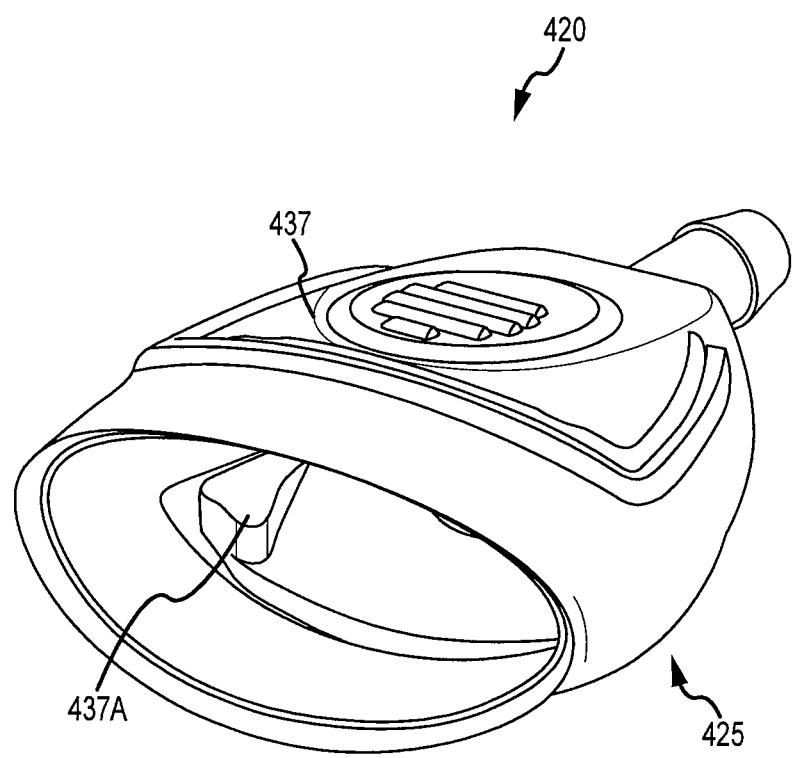
FIG. 37 is an isometric view of a female portion of a latch assembly according to certain embodiments.
Figure 38:
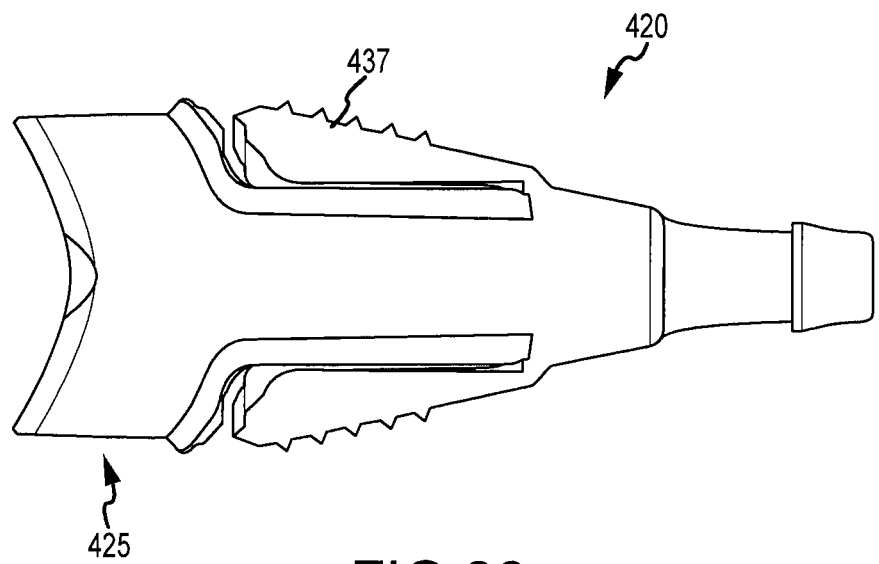
FIG. 38 is a left view of a female portion of a latch assembly according to certain embodiments.
Figure 39:
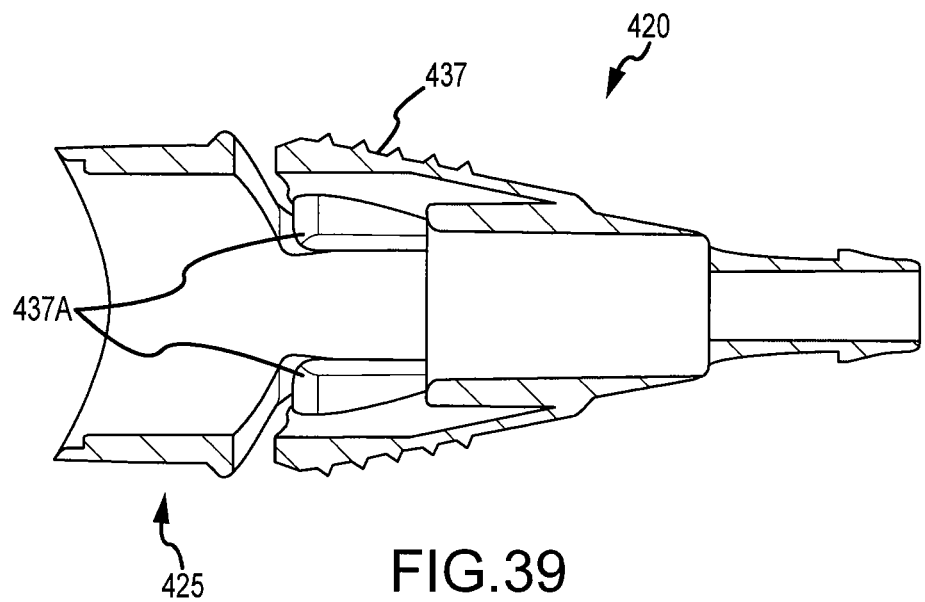
FIG. 39 is a left section view of a female portion of a latch assembly according to certain embodiments.
Figure 40:
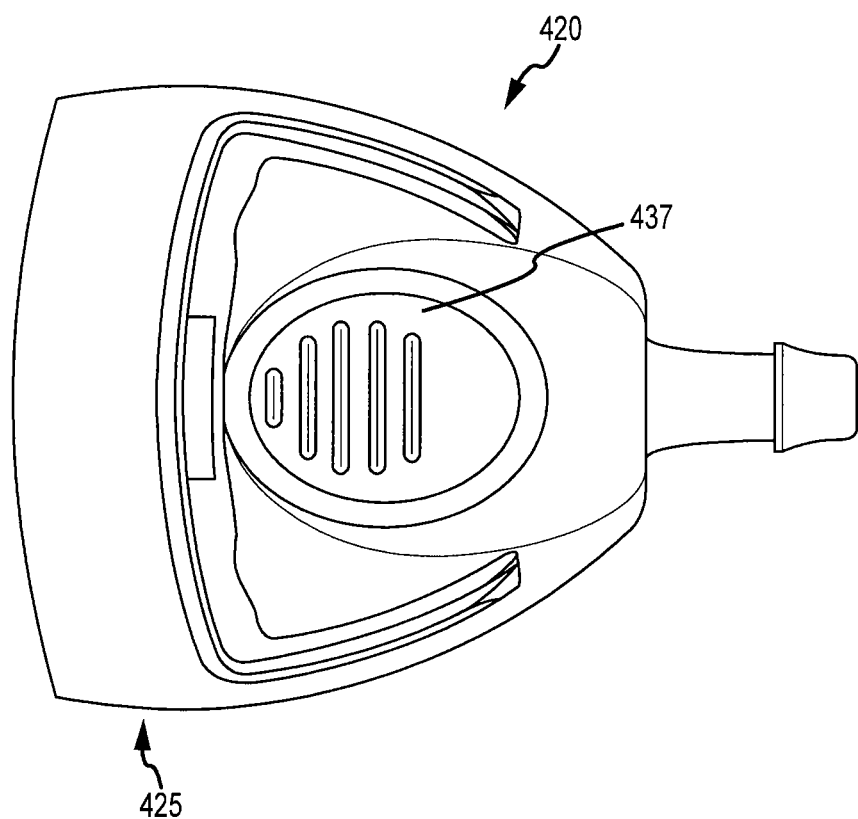
FIG. 40 is a top view of a female portion of a latch assembly according to certain embodiments.

As best shown in FIGS. 37 and 39, the inside surface of the release button 437 includes two raised protuberances 437A. These raised protuberances may be positioned in a corresponding location to the ramped engagement features 358 of the male portion 340. When releasing the male and female portions 340 and 420, as with latch assembly 300 and 100, the sloping surface of the ramped engagement feature 358 together with the downward force from the release button 437 creates a separation force such that when the ramped engagement feature 358 clears the bottom surface of the shell 425, the two portions 420 and 340 are biased toward separation. Thus a separate tensile force may not be required to separate the two portions 420 and 340. In addition to that provided by latch assemblies 100 and 300, however, the raised protuberances 437A of the female portion 420 further act to pinch the cantilevered regions 357 together. This pinching force further acts on the ramped engagement feather 358 to further bias the male portion 340 and female portion 420 toward separation and further causing a spring-out motion between the male and female portions.

Those skilled in the art will understand and appreciate that several modifications and variations exist within the scope of the present invention. For example, the hollow cross sections described could be partially solid while still accommodating a conduit and allowing for the deflection of the release buttons and other cantilevered actions. The cross section could, for example, actually form a conduit by providing a generally solid cross-section while providing a conduit passing through the cross section. As an additional example of a variation within the scope of the invention, the embodiments shown include two opposing release buttons while this could be limited to one release button or several release buttons could be provided. The molded-in slot could be cut out after molding or it could be a weakened area (e.g. thinner material). Alternatively, the whole surface of the shell could be flexibly deflectable and the slot could be omitted. Additionally, rather than elastically flexible cantilevered release buttons, the buttons could be hinged and spring loaded. Various shaped buttons could be provided to accommodate ergonomics or function of the device and would not have to match the contour of the shell. The release buttons have been described with four sides, but could be any shape and have various sides where one or two or even several are connected and the others are not to provide a cantilevered effect. As another example, the ramped engagement feature could be limited to a projection adapted to fit into a recess on the inside of a shell and various shapes of the projection could be included and matched to a recess formed in the shell.

The advantages of the latch assembly as described above include its ability to be quickly and easily engaged and released. The release buttons and engagement features of the described device may allow for efficient splicing of conduits by advancing the male and female portions toward one another and efficient release by pressing the release button. This is in contrast to threaded connections requiring alignment and time consuming twisting of the connections which often results in twisting of the conduits and tangling of the conduits.

Another advantage of the latch assembly described is the secure connection provided. In light of the efficiency discussed above relating to the ease with which the assembly can be spliced, the secure connection provided remains consistent with that necessary to avoid unwanted failure of a connection.

Another advantage of the latch assembly is the effectiveness of the connection provided. Also in light of the efficiency discussed above relating to the ease of use of the assembly, the latching nature of the device also provides for an effective connection in that the conduits are connected so as to minimize or eliminate unwanted leaks or escape of matter carried in the conduit.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

The invention claimed is:

1. A connector assembly for coupling together first and second fluid conduits, the assembly comprising
   a first connector including a proximal end for coupling with the first fluid conduit, a distal end opposite the proximal end, a fluid pathway between the proximal and distal ends, and a first housing extending about at least a portion of the fluid pathway, wherein
     the first housing has opposing major faces and peripheral sidewalls connecting the major faces; and
     the first housing defines a slot in each of the major faces open to an inner cavity within the first housing that at least partially defines a respective cantilevered release button within each of the major faces of the first housing extending distally to a free end of the cantilevered release button from a fixed end of the cantilevered release button; and
   a second connector including a proximal end for coupling with the second fluid conduit, a distal end opposite the proximal end, a fluid pathway between the proximal and distal ends, and a second housing extending about at least a portion of the fluid pathway, wherein
     the second housing has opposing major walls each defining a cantilevered region therein extending proximally to a free end of the cantilevered region from a fixed end of the cantilevered region with an engagement feature near the free end of the cantilevered region; and wherein
   when the distal ends of the connectors are moved towards each other in opposed fashion, the cantilevered regions pass underneath the slots to allow the engagement features to engage the slots and connect the first connector to the second connector.

2. A latch assembly for the connection of conduits, the latch assembly comprising
   a first connector including a first housing, a slot defined within a wall of the housing such that the slot is open to an inner cavity within the first housing, and a release button forming a part of the wall of the first housing and defined at least partially by the slot; and
   a second connector including a second housing that defines a cantilevered region within a wall of the second housing, the cantilevered region further having an engagement feature; wherein
   the cantilevered region is adapted to engage with the first housing of the first connector without deflecting the release button;
   the engagement feature is adapted to engage the slot; and
   the release button is adapted to disengage the engagement feature from the slot when depressed, thereby allowing separation of the female and male portions.

* * * * *